(12) United States Patent
Hughes et al.

(10) Patent No.: US 6,688,886 B2
(45) Date of Patent: Feb. 10, 2004

(54) SYSTEM AND METHOD FOR SEPARATING THREE-DIMENSIONAL MODELS

(75) Inventors: Joy Vannelia Hughes, Santa Cruz, CA (US); Daniel Stuart Russel, Stanford, CA (US); Huazhang Luo, Redwood City, CA (US); Carmen Cheang, Sunnyvale, CA (US); Elena Pavloskaia, San Francisco, CA (US); Venkata Sarva, Fremont, CA (US)

(73) Assignee: Align Technology, Inc., Santa Clara, CA (US)

( * ) Notice: Subject to any disclaimer, the term of this patent is extended or adjusted under 35 U.S.C. 154(b) by 302 days.

(21) Appl. No.: 09/847,904

(22) Filed: May 2, 2001

(65) Prior Publication Data

US 2002/0055081 A1 May 9, 2002

Related U.S. Application Data

(63) Continuation-in-part of application No. 09/539,021, filed on Mar. 30, 2000, now Pat. No. 6,371,761, and a continuation-in-part of application No. 09/539,185, filed on Mar. 30, 2000.

(51) Int. Cl.$^7$ .................................................. A61C 3/00
(52) U.S. Cl. ......................................................... 433/24
(58) Field of Search ............................ 433/24, 215, 223; 700/98, 118; 703/2

(56) References Cited

U.S. PATENT DOCUMENTS

| 3,660,900 | A | | 5/1972 | Andrews |
|---|---|---|---|---|
| 3,860,803 | A | | 1/1975 | Levine |
| 4,755,139 | A | | 7/1988 | Abbatte et al. |
| 4,798,534 | A | | 1/1989 | Breads |
| 4,837,732 | A | * | 6/1989 | Brandestini et al. ......... 433/223 |
| 4,856,991 | A | | 8/1989 | Breads et al. |
| 4,936,862 | A | | 6/1990 | Walker et al. |
| 5,035,813 | A | | 7/1991 | Breads et al. |
| 5,055,039 | A | | 10/1991 | Abbatte et al. |

(List continued on next page.)

OTHER PUBLICATIONS

Aftosmis, "Intesection of Generally Positioned Polygons in $R^3$" Downloaded from web on Aug. 14, 2000 <<http://george.arc.nasa.gov/~aftosmis/cart3d/bool_intersection.html>> p. 1.

Aftosmis, "Tie–breaking, Degeneracies and Floating Point Arithmetic" Downloaded from web on Apr. 28, 1999 >>http://george.arc.nasa.gov/~aftosmis/cart3d/degeneracy/degeneracy.html>>p. 1.

(List continued on next page.)

*Primary Examiner*—Todd E. Manahan
(74) *Attorney, Agent, or Firm*—Townsend and Townsend and Crew LLP; Bao Tran, Esq.

(57) ABSTRACT

A computer-implemented method separates first and second portions of a tooth by defining a cutting surface intersecting the first and second portions by specifying two points; and applying the cutting surface to the tooth to separate the tooth into two portions.

35 Claims, 30 Drawing Sheets

U.S. PATENT DOCUMENTS

| | | | |
|---|---|---|---|
| 5,059,118 A | 10/1991 | Breads et al. | |
| 5,139,419 A | 8/1992 | Andreiko et al. | |
| 5,186,623 A | 2/1993 | Breads et al. | |
| 5,273,429 A | 12/1993 | Rekow et al. | |
| 5,338,198 A | 8/1994 | Wu et al. | |
| 5,340,309 A | 8/1994 | Robertson | |
| 5,342,202 A | 8/1994 | Deshayes | |
| 5,368,478 A | 11/1994 | Andreiko et al. | |
| 5,382,164 A | 1/1995 | Stern | |
| 5,395,238 A | 3/1995 | Andreiko et al. | |
| 5,431,562 A | 7/1995 | Andreiko et al. | |
| 5,447,725 A | 9/1995 | Damani et al. | |
| 5,452,219 A | 9/1995 | Dehoff et al. | |
| 5,454,717 A | 10/1995 | Andreiko et al. | |
| 5,474,448 A * | 12/1995 | Andreiko et al. | 433/24 |
| 5,533,895 A | 7/1996 | Andreiko et al. | |
| 5,549,476 A | 8/1996 | Stern | |
| 5,587,912 A | 12/1996 | Andersson et al. | |
| 5,605,459 A | 2/1997 | Kuroda et al. | |
| 5,607,305 A | 3/1997 | Andersson et al. | |
| 5,645,421 A | 7/1997 | Slootsky | |
| 5,851,115 A * | 12/1998 | Carlsson et al. | 433/215 |
| 5,975,893 A * | 11/1999 | Chisti et al. | 433/24 |
| 6,371,761 B1 | 4/2002 | Cheang et al. | |

OTHER PUBLICATIONS

Bohm et al., "A survey of curve and surface methods in CAGD" Computer Aided Geometric Design (1984) 1.

Chiappone, "Constructing the Gnathologic Setup and Positioner" JCO, (Feb. 1980) vol. XIV No. 2, pp. 121.

Cottingham, "Gnathologic Clear Plastic Positioner" Am.J. Orthodontics, (Jan. 1969) vol. 55 No. 1, pp. 23.

Cureton, "Correcting Malaligned Mandibular incisors with Removable Retainers" J. Clin. Orthodon. (1996) 30:390.

Edelsbrunner et al., "Simulation of Simplicity: A Technique to Cope with Degenerate Cases in Geometric Algorithms" ACM Transactions on Graphics (1990) 9(1):66.

Kesling, "The Philosophy of the Tooth Positioning Appliance" Am J. Orthod. Oral Surg. (Jun. 1945) vol. 31, No. 6 pp. 297.

Kesling, "Coordinating the Predetermined Pattern and Tooth Positioner with Conventional Treatment" Am. J. Orthod. Oral Surg., (1946) 32:285.

Kleeman et al., "The Speed Positioner" JCO (Dec. 1996) vol. XXX, No. 12, p. 673.

Kuroda et al., "Three–Dimensional Dental Cast Analyzing System Using Laser Scanning" Am. J. Orthod. Dento. Orthop. (Oct. 1996) vol. 110, No. 4, p. 365.

Press et al., Numerical Recipes Dr. Dobb's Journal (DATE?) PAGES?.

"Adapting Vacuum Thermoforming Machines for Essix™"http://www.essix.com/magazine/default.html, Aug. 13, 1997.

Shilliday, "Minimizing Finishing Problems with the Mini–Positioner" Am. J. Orthodontics, (1971) 59:598.

Tru–Tain Orthodontic & Dental Supplies, AAOF Case Partner.

Warunek, et al., "Clinical Use of Silicone Elastomer Appliances" JCO (Oct. 1989) vol. XXIII, No. 10, pp. 694.

Wells, "Application of the Positioner Appliance in Orthodontic Treatment" Am. J. Orthodont (Oct. 1970) vol. 58, No. 4, pp. 351.

* cited by examiner

SYSTEM AND METHOD FOR SEPARATING THREE-DIMENSIONAL MODELS

CROSS-REFERENCES TO RELATED APPLICATIONS

This application is a continuation-in-part of U.S. Ser. No. 09/539,021, filed Mar. 30, 2000 now U.S. Pat. No. 6,371,761, entitled "Flexible Plane for Separating Teeth Models." The application is also a continuation-in-part of U.S. Ser. No. 09/539,185, filed Mar. 30, 2000, entitled "System for Separating Teeth Models." The full disclosures of each of these prior applications is incorporated herein by reference.

BACKGROUND OF THE INVENTION

1. Field of the Invention

The invention relates generally to the field of orthodontics and, more particularly, to computer-automated separation of a model of teeth.

2. Description of the Background Art

Tooth positioners for finishing orthodontic treatment are described by Kesling in the Am. J. Orthod. Oral. Surg. 31:297–304 (1945) and 32:285–293 (1946). The use of silicone positioners for the comprehensive orthodontic realignment of a patient's teeth is described in Warunek et al. (1989) J. Clin. Orthod. 23:694–700. Clear plastic retainers for finishing and maintaining tooth positions are commercially available from Raintree Essix, Inc., New Orleans, La. 70125, and Tru-Tain Plastics, Rochester, Minn. 55902. The manufacture of orthodontic positioners is described in U.S. Pat. Nos. 5,186,623; 5,059,118; 5,055,039; 5,035,613; 4,856,991; 4,798,534; and 4,755,139.

Other publications describing the fabrication and use of dental positioners include Kleemann and Janssen (1996) J. Clin. Orthodon. 30:673–680; Cureton (1996) J. Clin. Orthodon. 30:390–395; Chiappone (1980) J. Clin. Orthodon. 14:121–133; Shilliday (1971) Am. J. Orthodontics 59:596–599; Wells (1970) Am. J. Orthodontics 58:351–366; and Cottingham (1969) Am. J. Orthodontics 55:23–31.

Kuroda et al. (1996) Am. J. Orthodontics 110:365–369 describes a method for laser scanning a plaster dental cast to produce a digital image of the cast. See also U.S. Pat. No. 5,605,459.

U.S. Pat. Nos. 5,533,895; 5,474,448; 5,454,717; 5,447,432; 5,431,562; 5,395,238; 5,368,478; and 5,139,419, assigned to Ormco Corporation, describe methods for manipulating digital images of teeth for designing orthodontic appliances.

U.S. Pat. No. 5,011,405 describes a method for digitally imaging a tooth and determining optimum bracket positioning for orthodontic treatment. Laser scanning of a molded tooth to produce a three-dimensional model is described in U.S. Pat. No. 5,338,198. U.S. Pat. No. 5,452,219 describes a method for laser scanning a tooth model and milling a tooth mold. Digital computer manipulation of tooth contours is described in U.S. Pat. Nos. 5,607,305 and 5,587,912. Computerized digital imaging of the jaw is described in U.S. Pat. Nos. 5,342,202 and 5,340,309. Other patents of interest include U.S. Pat. Nos. 5,549,476; 5,382,164; 5,273,429; 4,936,862; 3,860,803; 3,660,900; 5,645,421; 5,055,039; 4,798,534; 4,856,991; 5,035,613; 5,059,118; 5,186,623; and 4,755,139.

BRIEF SUMMARY OF THE INVENTION

In one aspect, a computer-implemented method separates a plurality of three-dimensional polygonal objects, the objects having a plurality of edges. The method includes selecting two points on one or more objects; determining a piece-wise continuous curve on the surface of the objects based on the two points; and separating the objects based on the piece-wise continuous curve.

Implementations of the above aspect may include one or more of the following. The determining a piece-wise continuous curve on the surface of the three-dimensional polygonal objects may include determining a local curvature for each edge of each object; generating a cost function based on the local curvature and length of the edge; and determining the shortest path based on the cost function. The method also includes generating a set of control points to create a fitting surface based on the shortest path. The fitting surface can be used to separate the object into two portions. The fitting surface can be expressed as a function such as a spline function. The fitting surface can be interactively adjusted. The method includes interactively highlighting a separated portion such as a border of the portion. The generating the fitting surface includes identifying one or more points on the object. The method includes determining a shortest path between the points and the fitting surface. The method also includes minimizing the curvature along the fitting surface. The fitting surface can be adjusted by moving one or more points on the object. The cutting surface can be adjusted by moving one or more nodes. Alternatively, the cutting surface can be adjusted by: specifying a point on the cutting surface and between two nodes; and adjusting the point to vary the cutting surface. The object can be a tooth. The shortest path can be used to segment the object into two portions. The method also includes displaying a plane having a surface specified by a plurality of nodes; adjusting one or more nodes to modify the surface of the plane; and applying the plane to the object. A handle can be provided to adjust each orientation of the plane. The method includes adjusting one or more nodes further comprises dragging and dropping the one or more nodes. In one implementation where the object includes two joined teeth to be separated, the method includes receiving an initial digital data set representing the two joined teeth, representing the two joined teeth as a teeth mesh; applying a fitting surface to the teeth mesh; identifying an intersecting line between the teeth mesh and fitting surface; and generating two separated teeth based on the intersecting line. The method also includes rendering a three-dimensional (3D) graphical representation of the separated teeth. A human user can modify the graphical representation of the teeth.

In another aspect, a computer program, residing on a tangible storage medium, is used to determine a piece-wise continuous curve on the surface of a three-dimensional polygonal object, the object having a plurality of edges. The program includes executable instructions operable to cause a computer to: apply a local curvature calculation to each edge of the object; generate a cost function based on the local curvature and length of the edge; and determine the shortest path based on the cost function.

In another aspect, a method for use in separating a computer model of teeth includes receiving a data set that contains a 3D representation of one or more teeth, calculating a local curvature calculation for each edge of the teeth; generating a cost function based on the local curvature and length of the edge; determining the shortest path by minimizing the cost function; determining a fitting surface for the shortest path; and applying the fitting surface to the teeth to separate the teeth.

In yet another aspect, a computer-implemented method separates first and second portions of a tooth by defining a cutting surface intersecting the first and second portions by specifying two points; and applying the cutting surface to the tooth to separate the tooth into two portions.

BRIEF DESCRIPTION OF THE DRAWINGS

FIG. 5I is a flow chart illustrating a process for separating a teeth model.

DESCRIPTION OF THE SPECIFIC EMBODIMENTS

Figure 1:
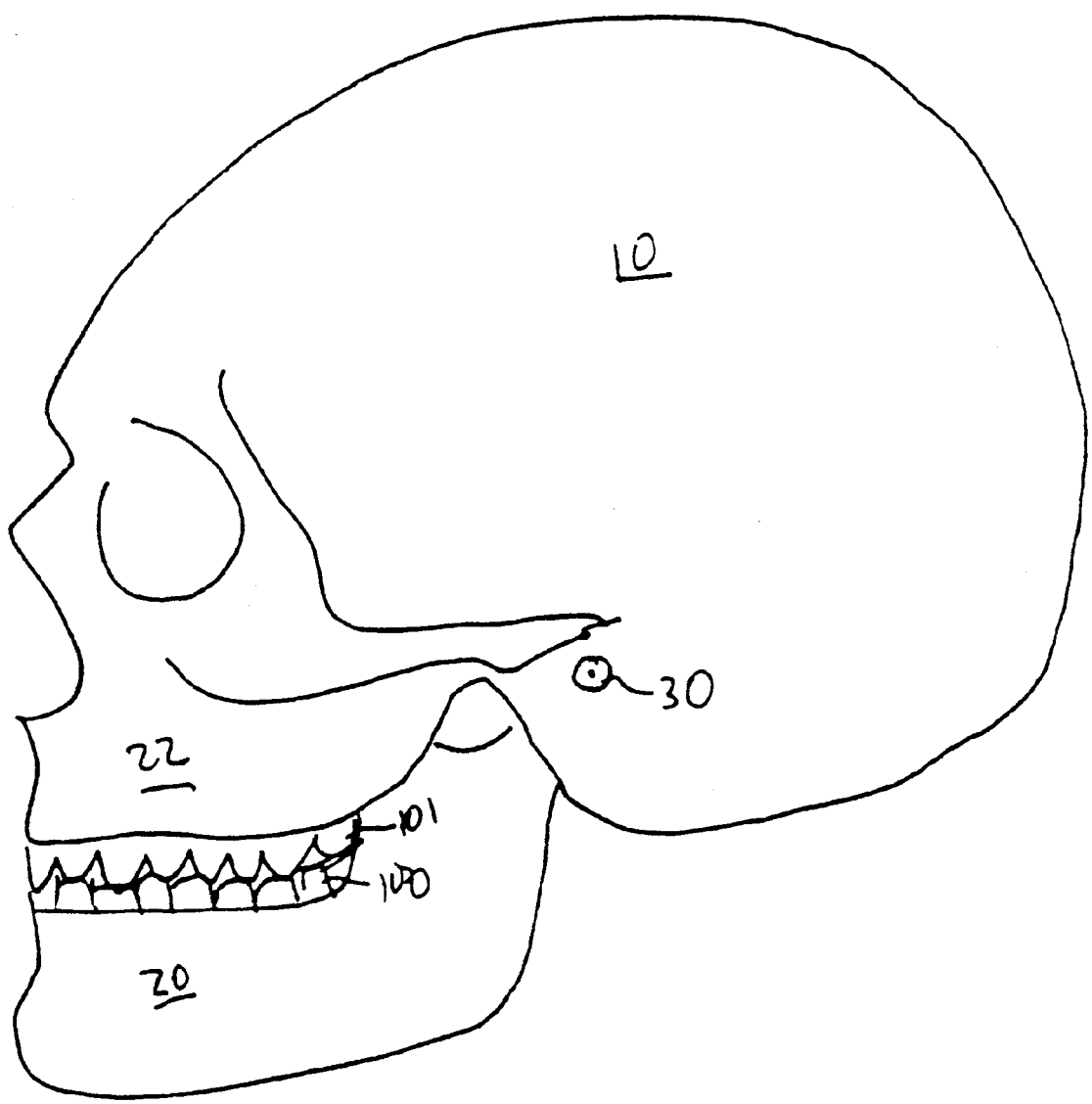
FIG. 1 illustrates a patient's jaw and provides a general indication of how teeth may be moved.

Referring now to FIG. 1, a representative jaw 100 includes sixteen teeth, at least some of which are to be moved from an initial tooth arrangement to a final tooth arrangement. To understand how the teeth may be moved, an arbitrary centerline (CL) is drawn through one of the teeth 102. With reference to this centerline (CL), the teeth may be moved in the orthogonal directions represented by axes 104, 106, and 108 (where 104 is the centerline). The centerline may be rotated about the axis 108 (root angulation) and 104 (torque) as indicated by arrows 110 and 112, respectively. Additionally, the tooth may be rotated about the centerline, as represented by arrow 114. Thus, all possible free-form motions of the tooth can be performed.

Figure 2:
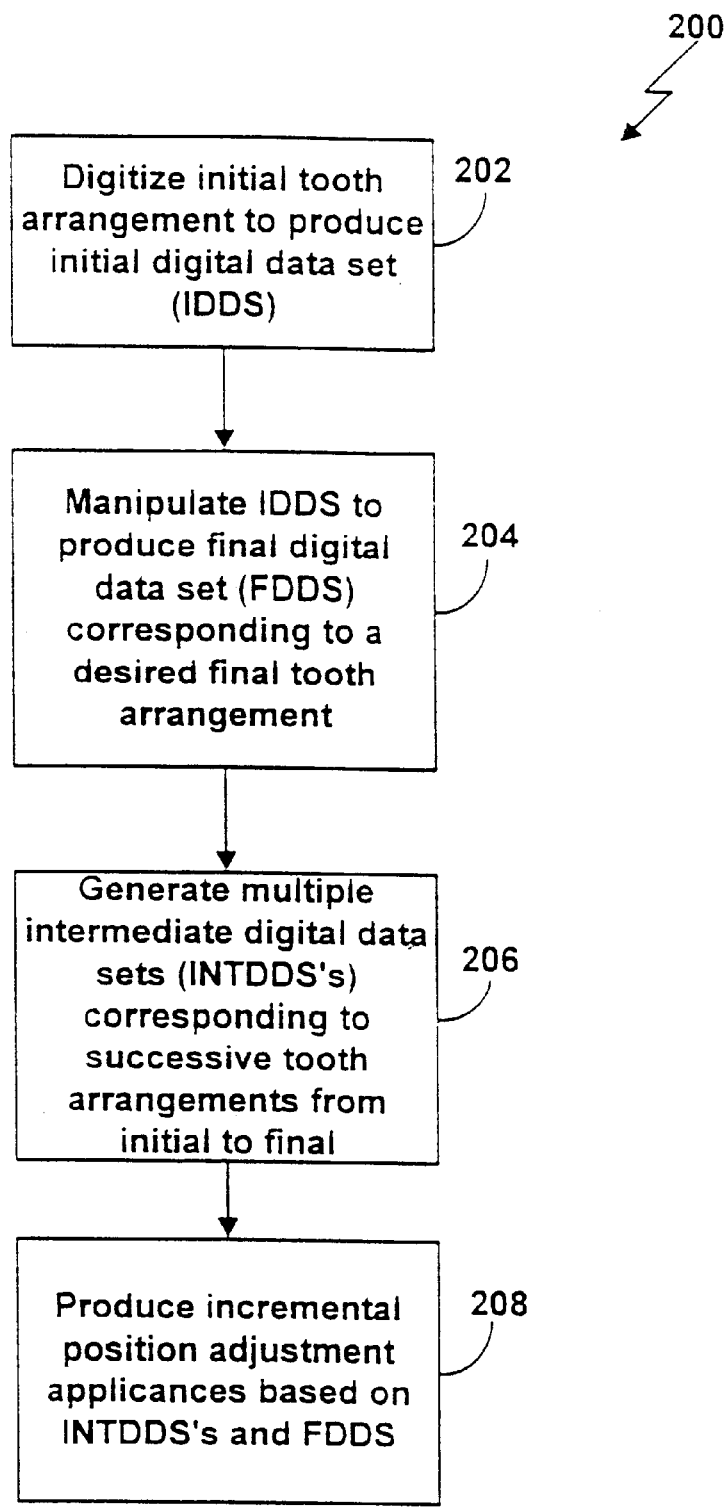
FIG. 2 is a block diagram illustrating steps for producing a system of incremental position adjustment appliances.

FIG. 2 shows a process 200 for producing the incremental position adjustment appliances for subsequent use by a patient to reposition the patient's teeth. As a first step, an initial digital data set (IDDS) representing an initial tooth arrangement is obtained (step 202). The IDDS may be obtained in a variety of ways. For example, the patient's teeth may be scanned or imaged using X-rays, three dimensional X-rays, computer-aided tomographic images or data sets, or magnetic resonance images, among others. More details on the contact or non-contact scanners are in commonly-owned and co-pending application Ser. No. 09/1169,276, filed Oct. 8, 1998, the content of which is incorporated by reference.

A plaster cast of the patient's teeth is obtained by well known techniques, such as those described in Graber, *Orthodontics: Principle and Practice*, Second Edition, Saunders, Pa., 1969, pp. 401–415. After the tooth casting is obtained, the casting is digitally scanned by a scanner, such as a non-contact type laser or destructive scanner or a contact-type scanner, to produce the IDDS. The data set produced by the scanner may be presented in any of a variety of digital formats to ensure compatibility with the software used to manipulate images represented by the data. In addition to the 3D image data gathered by laser scanning or destructive scanning the exposed surfaces of the teeth, a user may wish to gather data about hidden features, such as the roots of the patient's teeth and the patient's jaw bones. This information is used to build a detailed model of the patient's dentition and to show with more accuracy and precision how the teeth will respond to treatment. For example, information about the roots allows modeling of all tooth surfaces, instead of just the crowns, which in turn allows simulation of the relationships between the crowns and the roots as they move during treatment. Information about the patient's jaws and gums also enables a more accurate model of tooth movement during treatment. For example, an x-ray of the patient's jaw bones can assist in identifying ankylose teeth, and an MRI can provide information about the density of the patient's gum tissue. Moreover, information about the relationship between the patient's teeth and other cranial features allows accurate alignment of the teeth with respect to the rest of the head at each of the treatment steps. Data about these hidden features may be gathered from many sources, including 2D and 3D x-ray systems, CT scanners, and magnetic resonance imaging (MRI) systems. Using this data to introduce visually hidden features to the tooth model is described in more detail below.

The IDDS is manipulated using a computer having a suitable graphical user interface (GUI) and software appropriate for viewing and modifying the images. More specific aspects of this process will be described in detail below.

Individual tooth and other components may be segmented or isolated in the model to permit their individual repositioning or removal from the digital model. After segmenting or isolating the components, the user will often reposition the tooth in the model by following a prescription or other written specification provided by the treating professional. Alternatively, the user may reposition one or more teeth based on a visual appearance or based on rules and algorithms programmed into the computer. Once the user is satisfied, the final teeth arrangement is incorporated into a final digital data set (FDDS) (step 204).

The FDDS is used to generate appliances that move the teeth in a specified sequence. First, the centers of each tooth model may be aligned using a number of methods. One method is a standard arch. Then, the teeth models are rotated until their roots are in the proper vertical position. Next, the teeth models are rotated around their vertical axis into the proper orientation. The teeth models are then observed from the side, and translated vertically into their proper vertical position. Finally, the two arches are placed together, and the teeth models moved slightly to ensure that the upper and lower arches properly mesh together. The meshing of the upper and lower arches together is visualized using a collision detection process to highlight the contacting points of the teeth.

In step 204, final positions for the upper and lower teeth in a masticatory system of a patient are determined by generating a computer representation of the masticatory system. An occlusion of the upper and lower teeth is computed from the computer representation; and a functional occlusion is computed based on interactions in the computer representation of the masticatory system. The occlusion may be determined by generating a set of ideal models of the teeth. Each ideal model in the set of ideal models is an abstract model of idealized teeth placement which is customized to the patient's teeth, as discussed below. After applying the ideal model to the computer representation, and the position of the teeth is optimized to fit the ideal model. The ideal model may be specified by one or more arch forms, or may be specified using various features associated with the teeth.

Based on both the IDDS and the FDDS, a plurality of intermediate digital data sets (INTDDSs) are defined to correspond to incrementally adjusted appliances (step 206). Finally, a set of incremental position adjustment appliances are produced based on the INTDDs and the FDDS (step 208).

Figure 3:
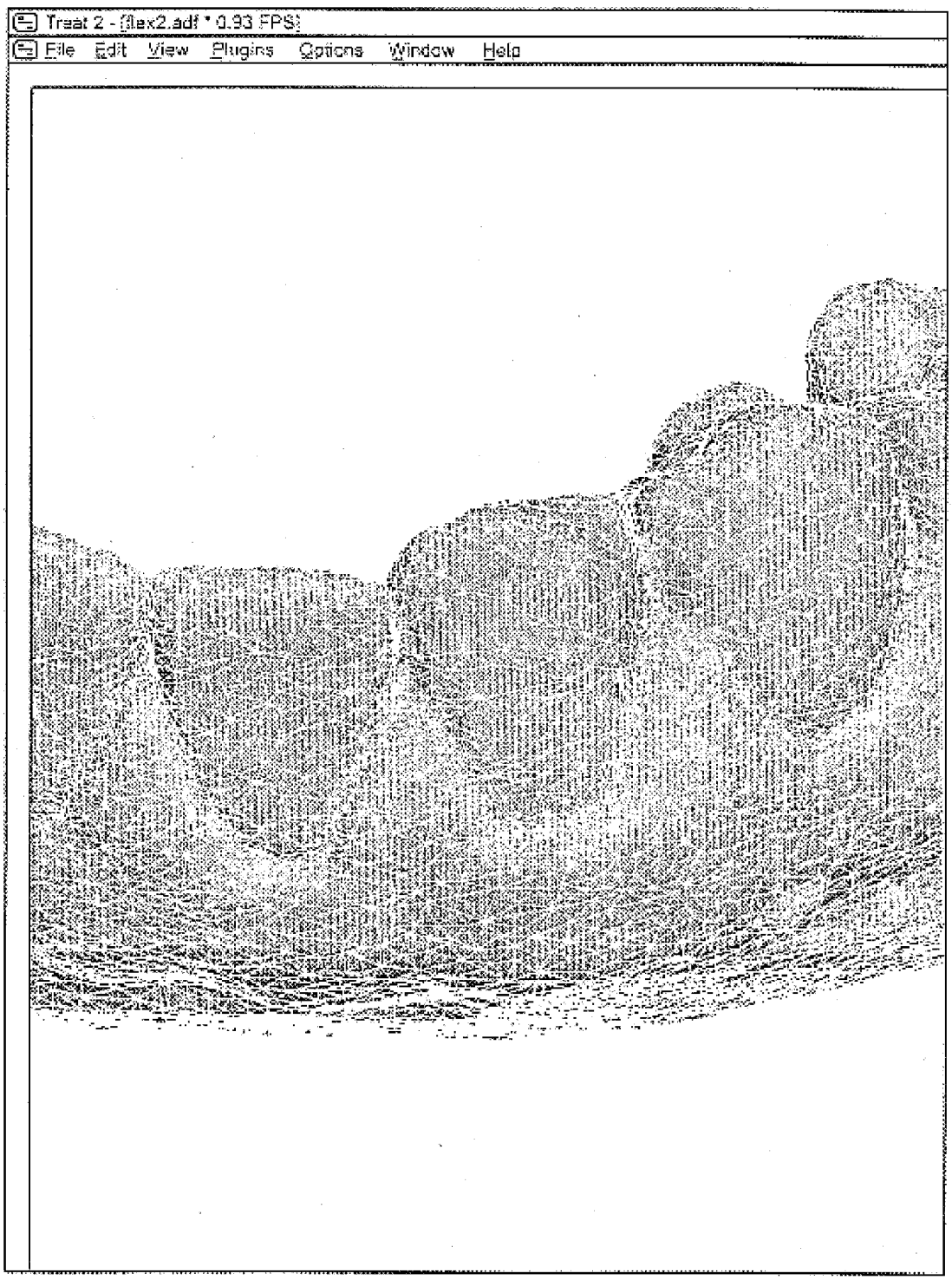
FIG. 3 is an illustration of a 3D model of teeth using triangular meshes.

FIG. 3 shows one exemplary 3D surface model of the teeth. The surface topology of a 3D model of teeth on a jaw can be modeled as a set of polygons of appropriate sizes and shapes joined at their edges. The set of polygons defining the 3D object is referred to as the "model" or "mesh" for the 3D object. In one embodiment, the polygons are triangles. In this embodiment, a triangle mesh is a piecewise linear surface with triangular faces joined along their edges.

Many types of scan data, such as that acquired by an optical scanning system, provide a 3D geometric model (e.g., a triangular surface mesh) of the teeth when acquired. Other scanning techniques, such as the destructive scanning technique described above, provide data in the form of volume elements ("voxels") that can be converted into a digital geometric model of the tooth surfaces. In one implementation, a marching cubes algorithm is applied to convert the voxels into a mesh, which can undergo a smoothing operation to reduce the jaggedness on the surfaces of the tooth model caused by the marching cubes conversion. One smoothing operation moves individual triangle vertices to positions representing the averages of connected neighborhood vertices to reduce the angles between triangles in the mesh.

Another optional step is the application of a decimation operation to the smoothed mesh to eliminate data points, which improves processing speed. After the smoothing and decimation operation have been performed, an error value is calculated based on the differences between the resulting mesh and the original mesh or the original data, and the error is compared to an acceptable threshold value. The smoothing and decimation operations are applied to the mesh once again if the error does not exceed the acceptable value. The last set of mesh data that satisfies the threshold is stored as the tooth model.

The triangles in FIG. 3 form a connected graph. In this context, two nodes in a graph are connected if there is a sequence of edges that forms a path from one node to the other (ignoring the direction of the edges). Thus defined, connectivity is an equivalence relation on a graph: if triangle A is connected to triangle B and triangle B is connected to triangle C, then triangle A is connected to triangle C. A set of connected nodes is then called a patch. A graph is fully connected if it consists of a single patch. The processes discussed below keep the triangles connected.

The mesh model can also be simplified by removing unwanted or unnecessary sections of the model to increase data processing speed and enhance the visual display. Unnecessary sections include those not needed for creation of the tooth repositioning appliance. The removal of these unwanted sections reduces the complexity and size of the digital data set, thus accelerating manipulations of the data set and other operations. After the user positions and sizes the eraser tool and instructs the software to erase the unwanted section, all triangles within the box set by the user are removed and the border triangles are modified to leave a smooth, linear border. The software deletes all of the triangles within the box and clips all triangles that cross the border of the box. This requires generating new vertices on the border of the box. The holes created in the model at the faces of the box are retriangulated and closed using the newly created vertices.

In alternative embodiments, the computer automatically simplifies the digital model by performing the user-oriented functions described above. The computer applies knowledge of orthodontic relevance to determine which portions of the digital model are unnecessary for image manipulation.

Once a 3D model of the tooth surfaces has been constructed, models of the patient's individual teeth can be derived. In one approach, individual teeth and other components are "cut" using a cutting tool to permit individual repositioning or removal of teeth in or from the digital data. After the components are "freed," a prescription or other written specification provided by the treating professional is followed to reposition the teeth. Alternatively, the teeth may be repositioned based on the visual appearance or based on rules and algorithms programmed into the computer. Once an acceptable final arrangement has been created, the final tooth arrangement is incorporated into a final digital data set (FDDS).

Figure 4:
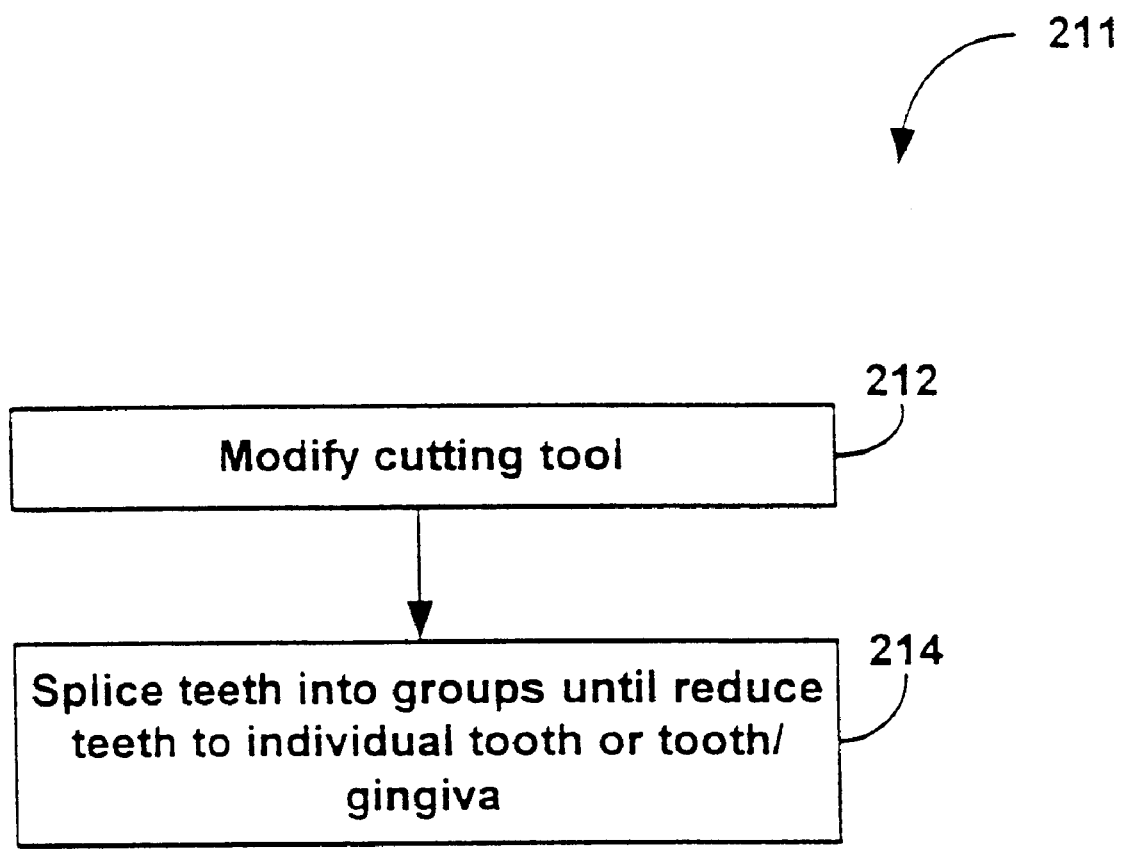
FIG. 4 is a flow chart illustrating a process for repetitively separating a group of teeth into two groups of teeth.

Referring now to FIG. 4, a process 211 for separating all teeth into individual units is shown. First, the process 211 customizes a cutting tool (step 212). Next, using the cutting tool, the user or an automated process applies the cutting tool to repetitively break up the group of teeth into two smaller groups until the teeth have been reduced into an individual unit (step 214). A viewer program displays an initial image of the teeth and, if requested by the user, an image of the separated teeth. The user can rotate the images in three dimensions to view the various tooth surfaces, and the clinician can snap the image to any of several predefined viewing angles. These viewing angles include the standard front, back, top, bottom and side views, as well as orthodontic-specific viewing angles, such as the lingual, buccal, facial, occlusal, and incisal views.

A saw tool is used to define the individual teeth (or possibly groups of teeth) to be moved. The tool separates the scanned image into individual geometric components enabling the software to move the tooth or other component images independent of remaining portions of the model. In one embodiment, the saw tool defines a path for cutting the graphic image by using two cubic B-spline curves lying in space, possibly constrained to parallel planes, either open or closed. A set of lines connects the two curves and shows the user the general cutting path. The user may edit the control points on the cubic B-splines, the thickness of the saw cut, and the number of erasers used, as described below.

In an alternative embodiment, the teeth are separated by using the saw as a "coring" device, cutting the tooth from above with vertical saw cuts. The crown of the tooth, as well as the gingivae tissue immediately below the crown are separated from the rest of the geometry, and treated as an individual unit, referred to as a tooth. When this model is moved, the gingivae tissue moves relative to the crown, creating a first order approximation of the way that the gingivae will reform within a patient's mouth.

Each tooth may also be separated from the original trimmed model. Additionally, a base may be created from the original trimmed model by cutting off the crowns of the teeth. The resulting model is used as a base for moving the teeth. This facilitates the eventual manufacture of a physical mold from the geometric model, as described below.

Thickness: When a cut is used to separate a tooth, the user will usually want the cut to be as thin as possible. However, the user may want to make a thicker cut, for example, when shaving down surrounding teeth, as described above. Graphically, the cut appears as a curve bounded by the thickness of the cut on one side of the curve.

Number of Erasers: A cut is comprised of multiple eraser boxes arranged next to each other as a piecewise linear approximation of the Saw Tool's curve path. The user chooses the number of erasers, which determines the sophistication of the curve created: the greater the number of segments, the more accurately the cutting will follow the curve. The number of erasers is shown graphically by the number of parallel lines connecting the two cubic B-spline curves. Once a saw cut has been completely specified the user applies the cut to the model. The cut is performed as a sequence of erasings, as shown in FIG. 4A. FIG. 4B shows a single erasing iteration of the cut as described in the algorithm for a open ended B-spline curve. For a vertical cut, the curves are closed, with $P_A[O]$ and $P_A[S]$ being the same point and $P_B[O]$ and $P_B[S]$ being the same point.

In one embodiment, the software automatically partitions the saw tool into a set of erasers based upon a smoothness measure input by the user. The saw is adaptively subdivided until an error metric measures the deviation from the ideal representation to the approximate representation to be less than a threshold specified by the smoothness setting. One error metric compares the linear length of the subdivided curve to the arclength of the ideal spline curve. When the difference is greater than a threshold computed from the smoothness setting, a subdivision point is added along the spline curve.

A preview feature may also be provided in the software. The preview feature visually displays a saw cut as the two surfaces that represent opposed sides of the cut. This allows the user to consider the final cut before applying it to the model data set.

Figure 5A:
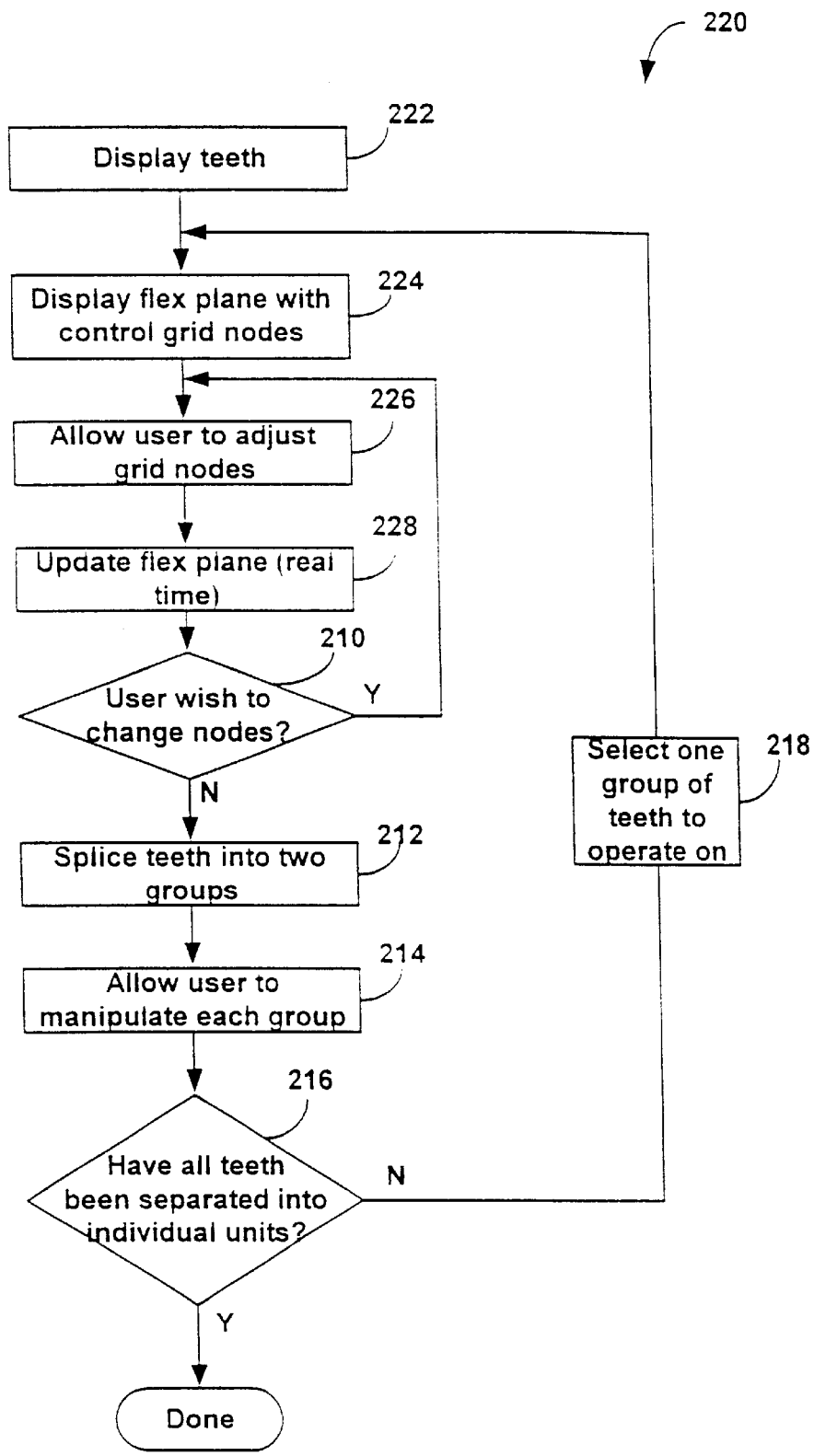
FIG. 5A is a flow chart illustrating a first process for displaying and applying a flexible plane for separating a teeth model.

FIG. 5A shows a process 220 that applies a flexible plane to splice two more teeth into two groups of teeth. First, the process displays one or more teeth for the user to review (step 222). Next, the process 220 displays a flexible plane with a plurality of control grid nodes (step 224). The flexible plane is formed by a number of surface patches called bicubic Bézier patches. The equation of such patch is well known, and it can be described as:

$$S(u, v) = \sum_{i=0}^{3} \sum_{k=0}^{3} b_{i,k} B_k^m(u) B_i^n(v)$$

where u, and v are coordinates in 3D space chosen along a straight plane between the two teeth, and S is the function along the ortho-normal direction to the straight plane, $b_{1,k}$ represents a Bézier point of the patch, and $B_1^n(t) = {}_nC_i(1-t)^{n-1}t^1, i=0,1,\ldots,n$ denotes the Bernstein polynomials.

The process 220 then accepts user adjustments to the position of various grid nodes to modify the flexible plane (step 226). The cutting curve and tooth portions associated with a flexible plane is then updated in real time (step 228).

The process 220 determines whether the user wishes to change the grid nodes to adjust the flexible plane. If so, the process 220 loops back to step 226 to continue adjusting the flex plane. Alternatively, the process 220 proceeds to splice the group of teeth into two smaller groups (step 212). Next, the process 220 allows the user to visually manipulate each of the smaller groups of teeth (step 214). In step 216, the process 220 determines whether all teeth have been separated into individual tooth (step 216). If not, the process 220 selects one group of teeth to operate on (step 218) and loops back to step 224 to allow the user to continue breaking the group of teeth until all teeth have been reduced to individual tooth that is ready for manipulation.

Figure 5B:
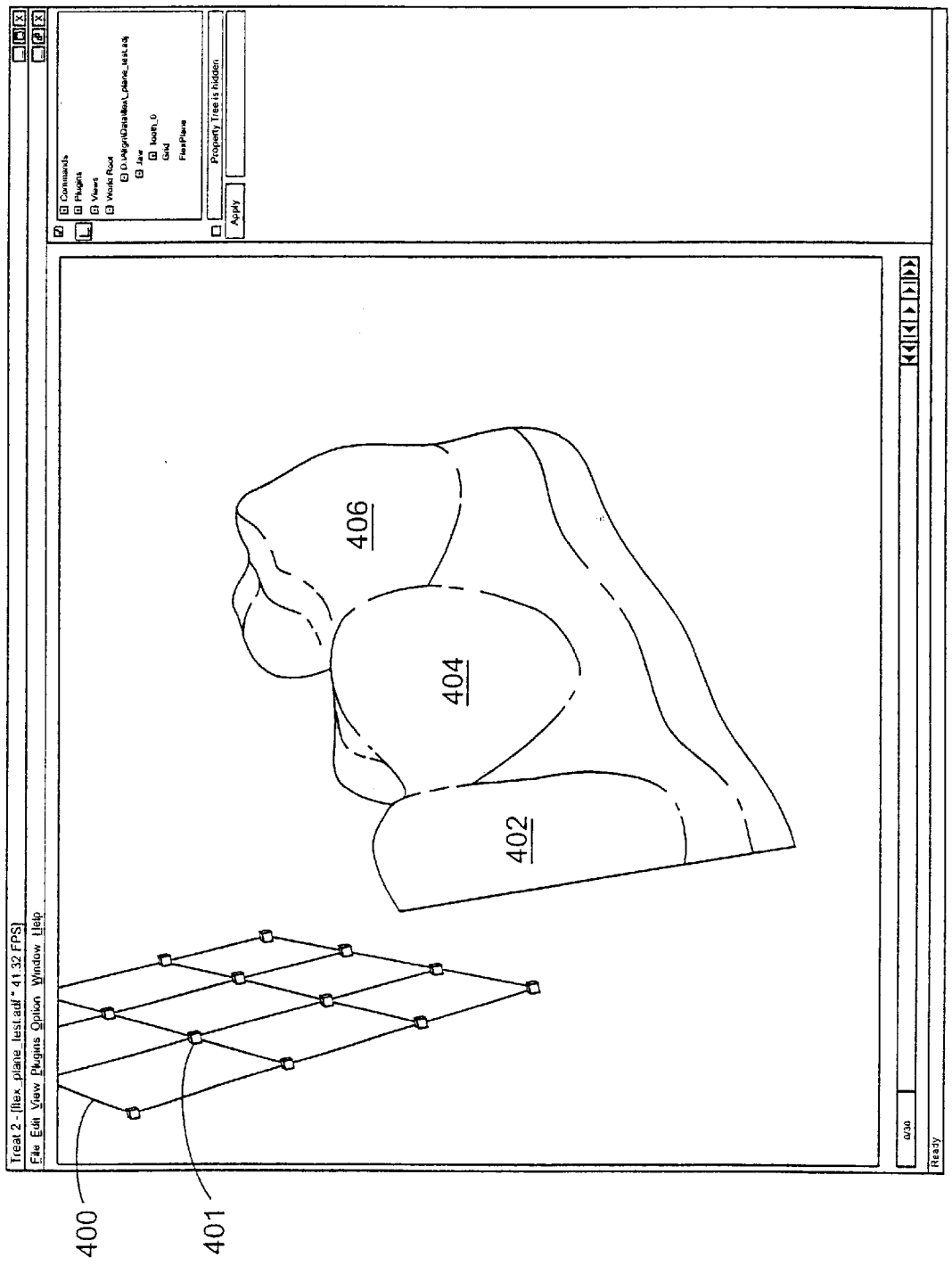
FIGS. 5B–5H show exemplary graphical user interfaces (GUI) for applying the flexible plane during the separation of a teeth model.

FIGS. 5B–5H show exemplary graphical user interfaces (GUI) for applying the flexible plane during the separation of a teeth model. FIG. 5B shows a flexible plane 400 with a plurality of nodes 401. In this example, the plane 400 is a 4×4 grid with sixteen nodes. FIG. 5B also shows a computer model for three teeth 402–406 which needs to be separated.

Figure 5C:
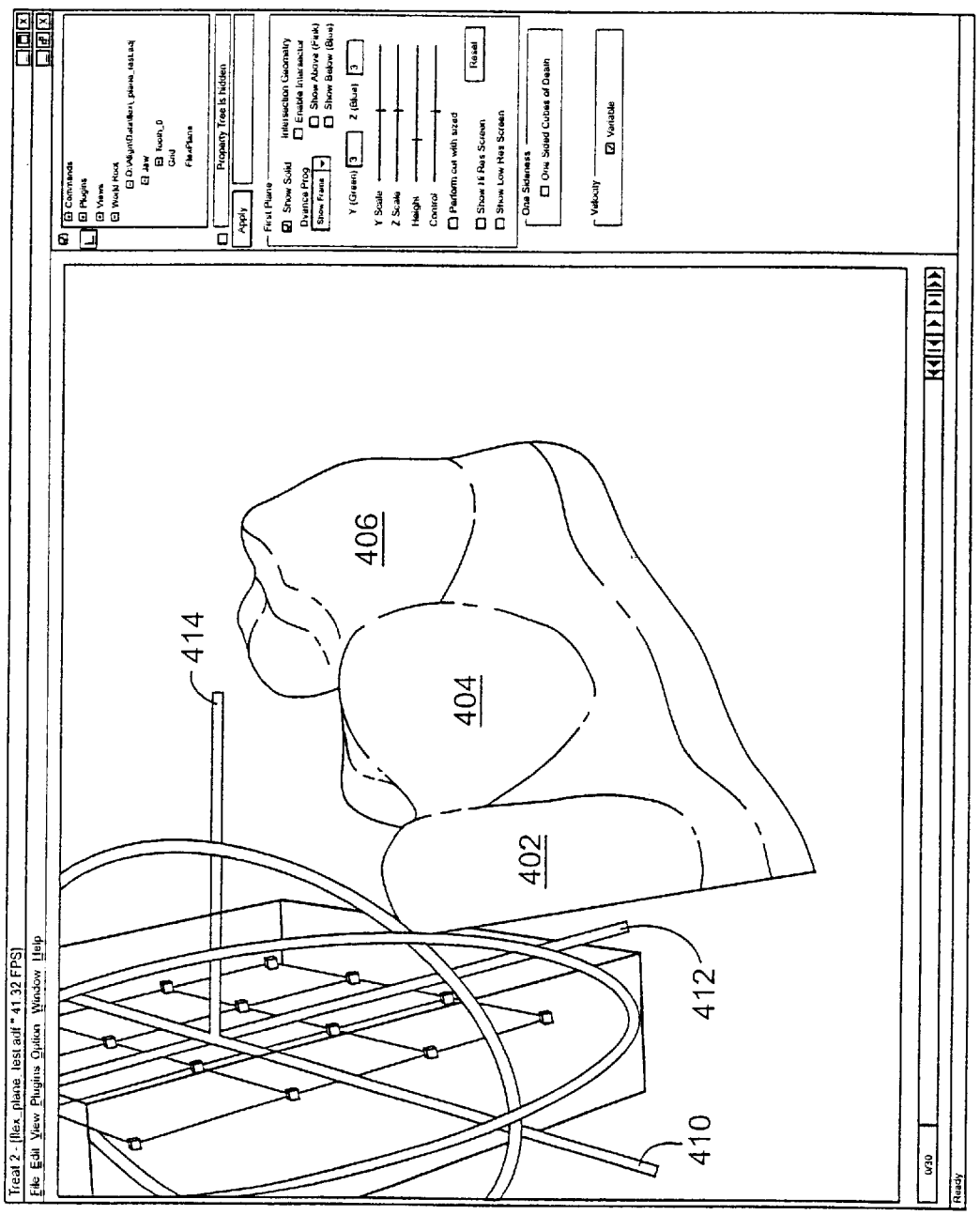

FIG. 5C shows a user interface for selecting the plane 400. The user can select the plane 400 by clicking on the plane 400. Once selected, the plane shows handles 410–414 that allow the user to maneuver the plane 400 in 3D space. The user can drag the plane 400 over the computer model of teeth 402–406.

Figure 5D:
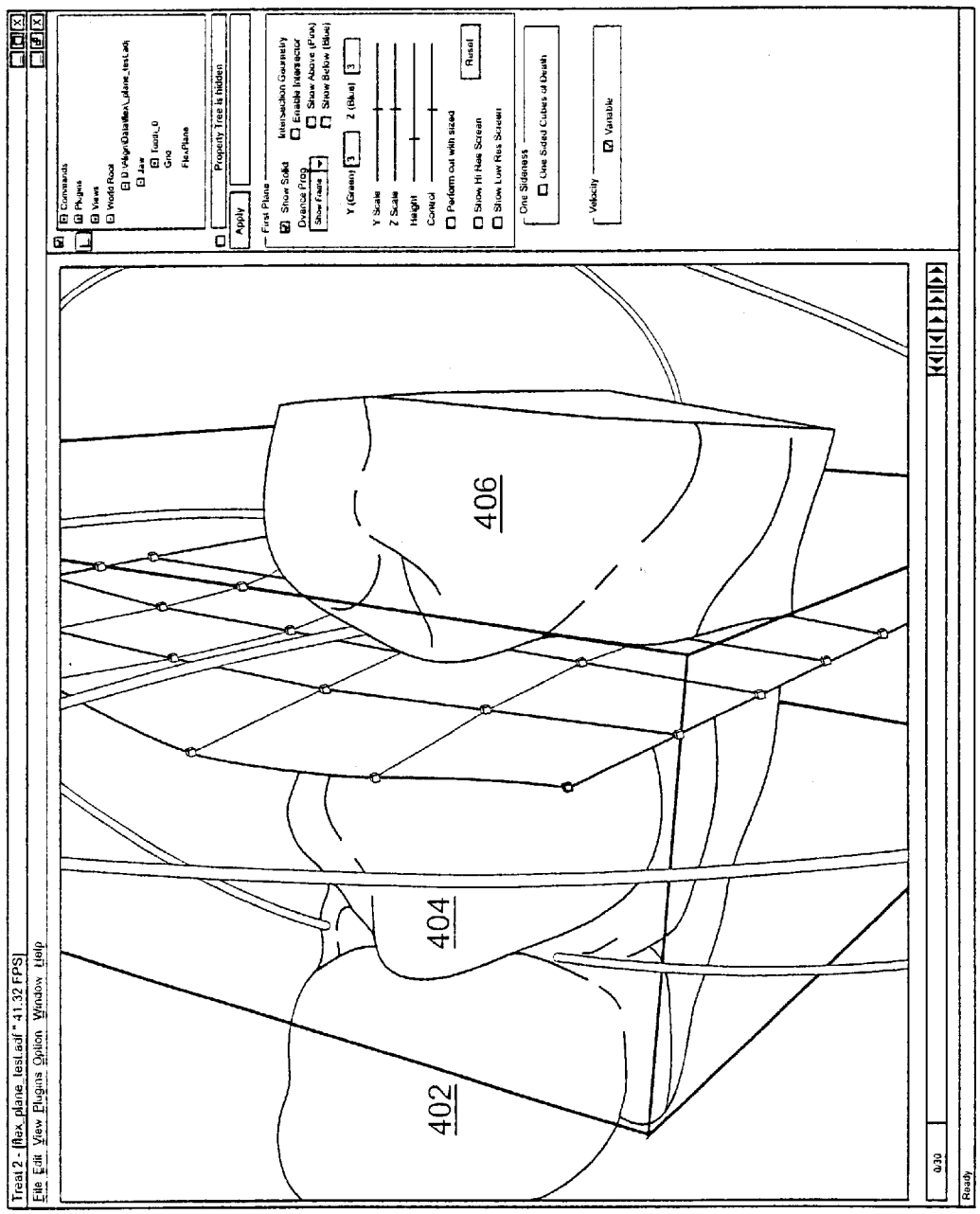

FIG. 5D shows the placement of the plane 400 between the teeth 404–406. The plane can be adjusted by dragging the nodes 401 so that the plane best fits a contour separating the teeth 404–406. Once the plane 400 has been adjusted to a desirable position, the user actives a teeth cutter engine, which separates the tooth, as described in more details in FIG. 6 below.

Figure 5E:
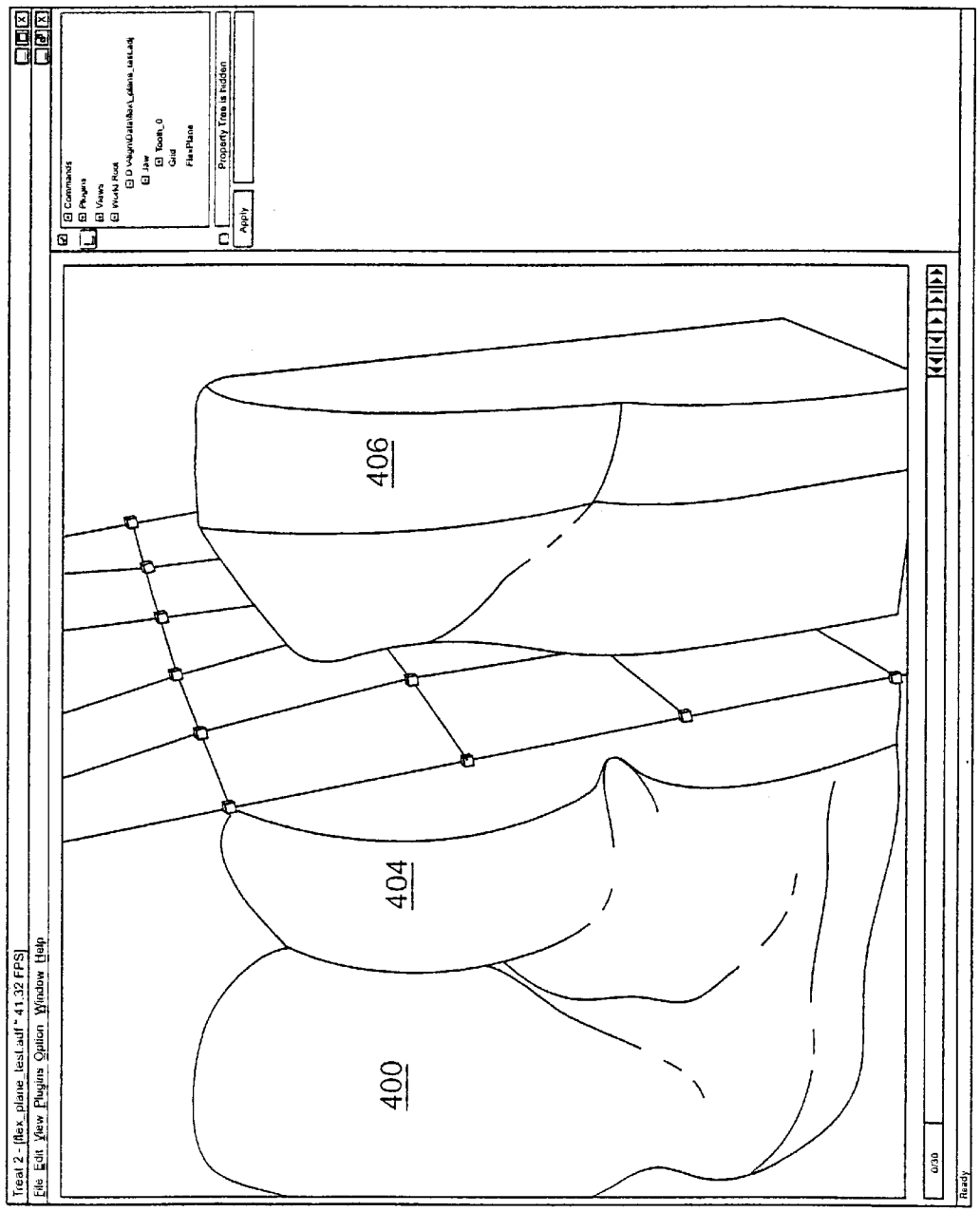
Figure 5F:
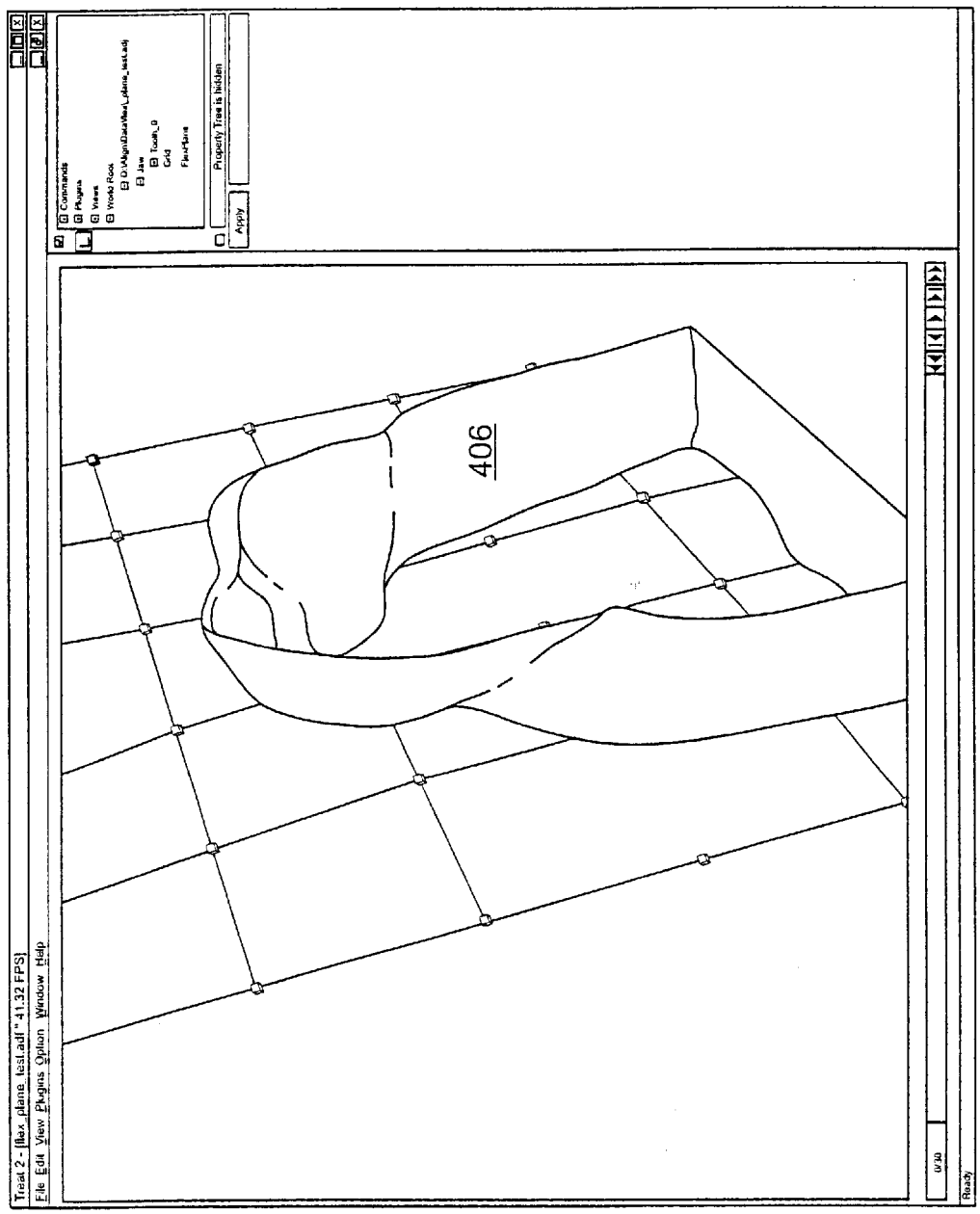
Figure 5G:
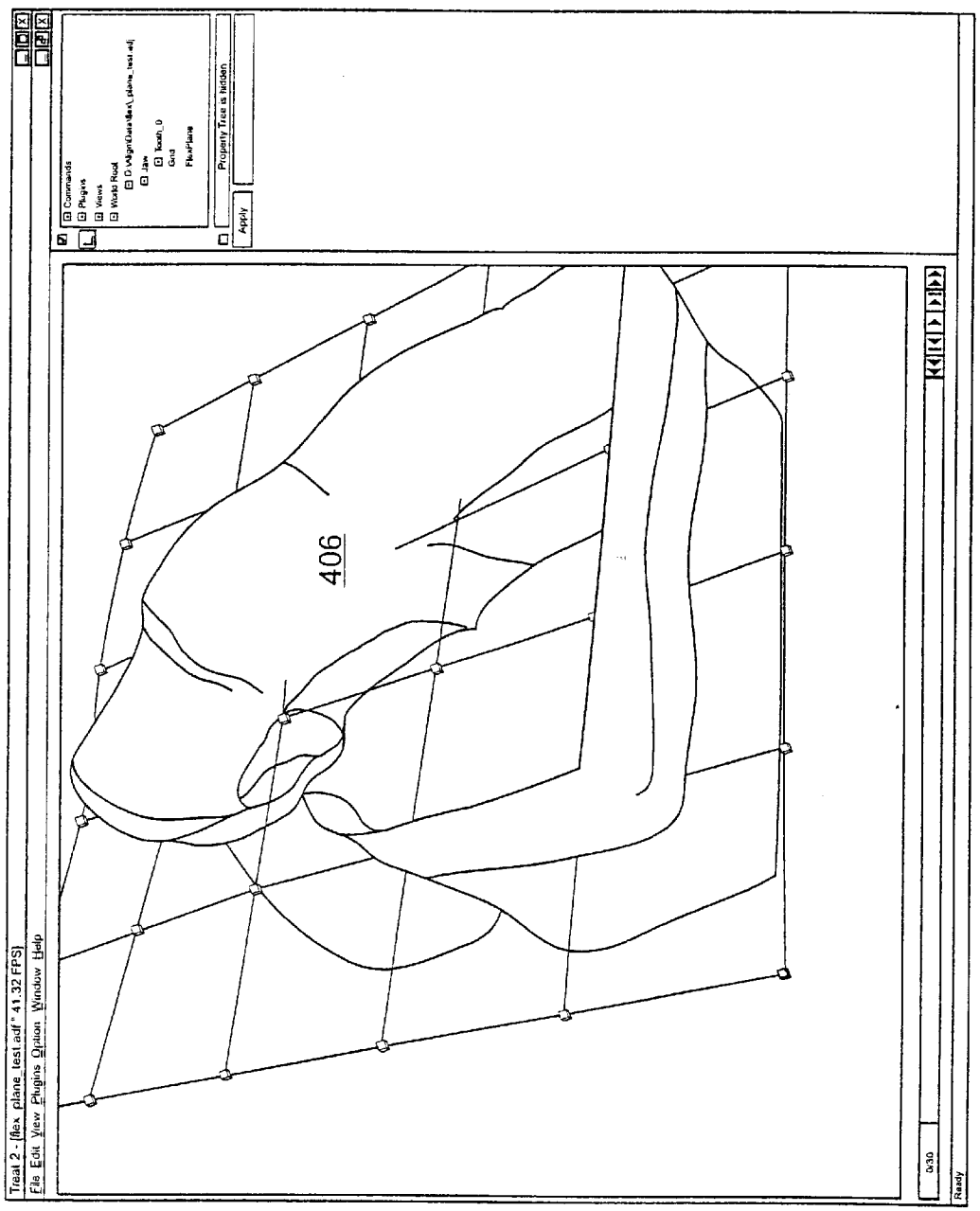
Figure 5H:
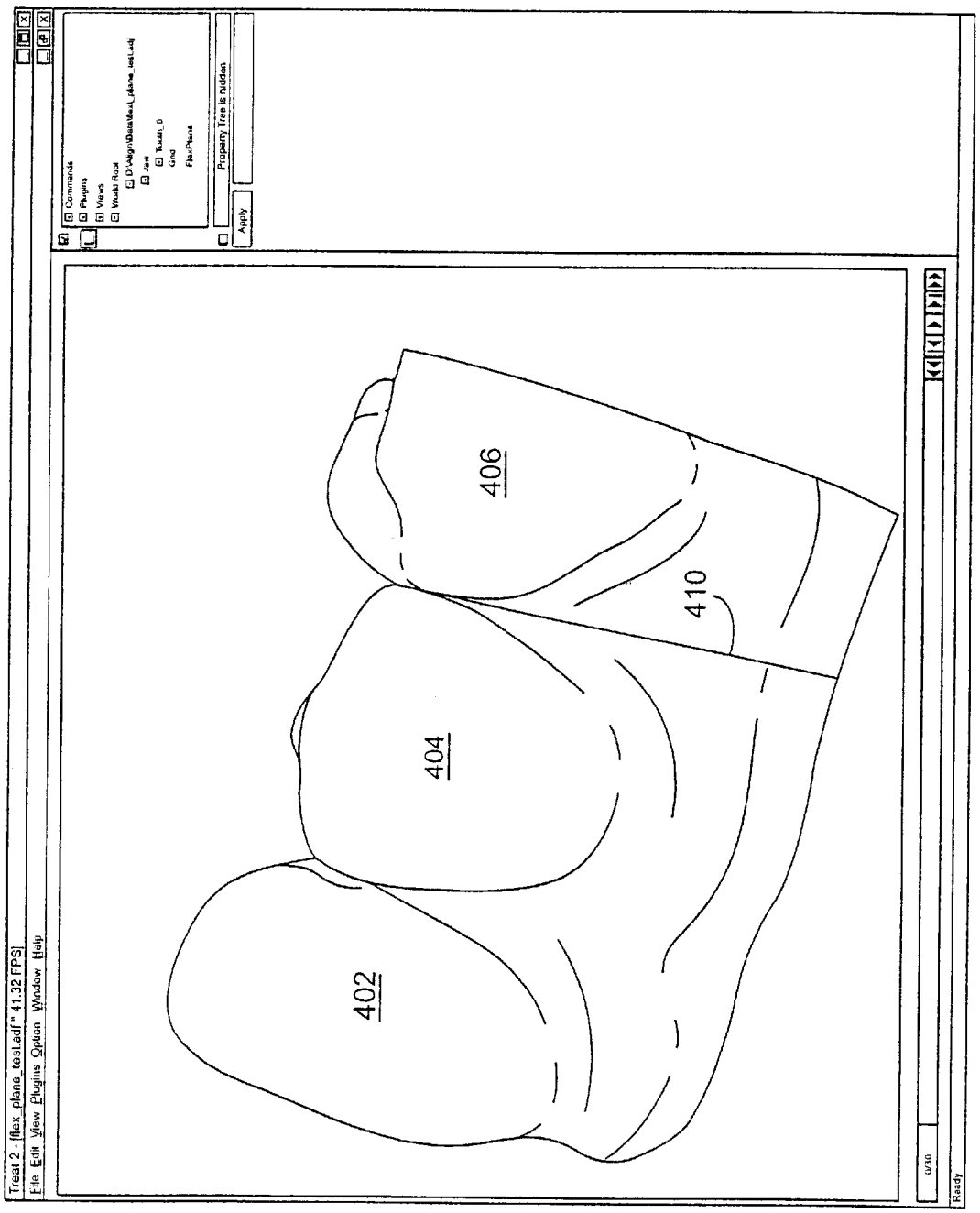
Figure 51:
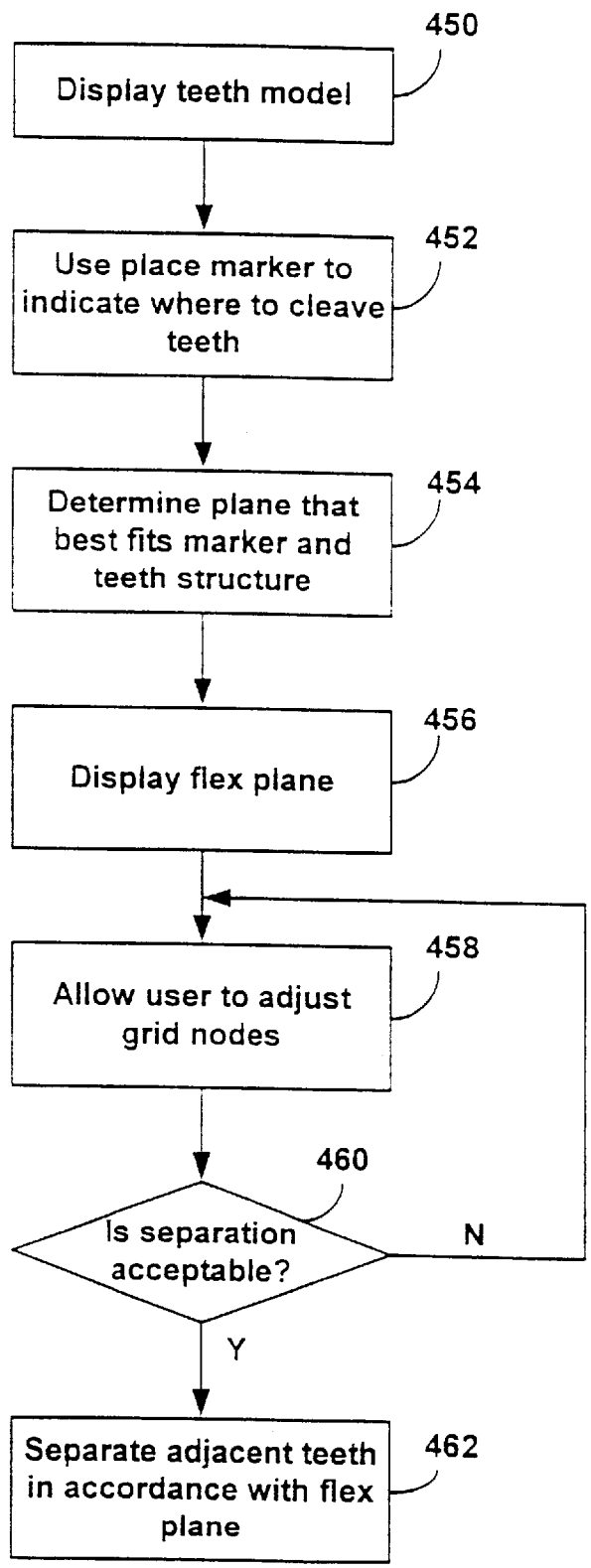

FIG. 5E shows the separation of teeth 404–406, while FIGS. 5F–5G show a border portion of the separated tooth 406 in conjunction with the plane 400. FIG. 5H shows a combined view of the teeth 402–406, with a separation line 410 between the tooth 404 and the tooth 406. The system can also fill in the side being cut so that all surfaces of the tooth can be realistically previewed.

FIG. 5I is a flow chart illustrating a second process for separating a teeth model. This process differs from the process of FIG. 5A in that the user specifies one or more markers where he or she expects the teeth to be separated, and the process of FIG. 5I would automatically fit the flexible plane to the markers.

First, a model of the teeth is displayed (step 450). Next, the user places one or more markers along a potential demarcation of the teeth (step 452). The process of FIG. 5I then determines the plane that best fits the markers and teeth structure (step 454). A flexible plane is then displayed over the demarcation of the teeth (step 456). The flexible plane includes a plurality of grid nodes that allow the user to adjust the plane if necessary.

The user can add nodes on the flexible plane, or can adjust the flexible plane by adjusting the nodes on the teeth (step 458). This adjustment can be performed iteratively (step 460) until a good fit is found. Once the user is satisfied with the flexible plane as a demarcation of the separated teeth, the process of FIG. 5I separates the teeth into individual teeth (step 462).

Pseudo code for operations to fit the plane 400 to the specified nodes of FIG. 5I is shown below:

assume: array pickpoints[ ] is of size N
  currently FlexPlane is formed by M(=sizeU×sizeV) Bézier patches
  function construct From Pick Point( ):
  (1) Fit a plane surface to pickPoints to give general direction of FlexPlane. This would define the U, V parametric space of FlexPlane.
  (2) For each pickPoints find its (u, v) coordinate by projecting it to the plane surface found in (1).
  (3) Form linear system of equation A (a N×M matrix) for least square minimization, where $$a_{ij}=e_1(u_1, v_1), \text{ where } 1<=i<=N, 1<=j<=M$$

where $e_j$ (u,v) is the basis function for an individual Bézier patch.
Also form b (a vector of size N), where $b_1$ is the $i^{th}$ pickPoints' distance to the plane surface in (1). The resulting linear system A*x=b, where x is the coefficients for each basis functions, is most often a rectangular system (i.e., the number of unknown are not the same as equations).
  (4) Following the application of the least square method, for the rectangular system in (3), multiply A'(the transpose of A) to both side of the equation to make it square. Yet the new system has multiple solutions in some cases, and no solution in other cases. To choose a particular solution, the following step is added.
  (5) Add a curvature constraint factor to the linear system. The curvature function is defined as $$C_{i,j} = \sum_{i=1}^{N}\sum_{j=1}^{M}\{(2x_{i,j}-x_{i,j-1}-x_{i,j+1})^2 + (2x_{i,j}-x_{i-1,j}-x_{i+1,j})^2\}.$$

The curvature matrix Q is then formed by the derivative of the curvature function. So the linear system of equation now becomes:

$$(A^tA+\delta Q)x=A^tb,$$

where $\delta$ is a user defined factor for the control of the curviness of the FlexPlane.
  (6) Solve the linear system in (5) using Cholesky factorization method. The resulting x value is used to update the FlexPlane surface.
  (7) Calculate the mean square error of the estimation by $$error_1=\|pickPoint_1 - FlexPlane(u_1, v_1)\|^2,$$

if the maximum error is greater then a pre-defined tolerance, then increase sizeU and sizeV and go to step (2).

Figure 5J:
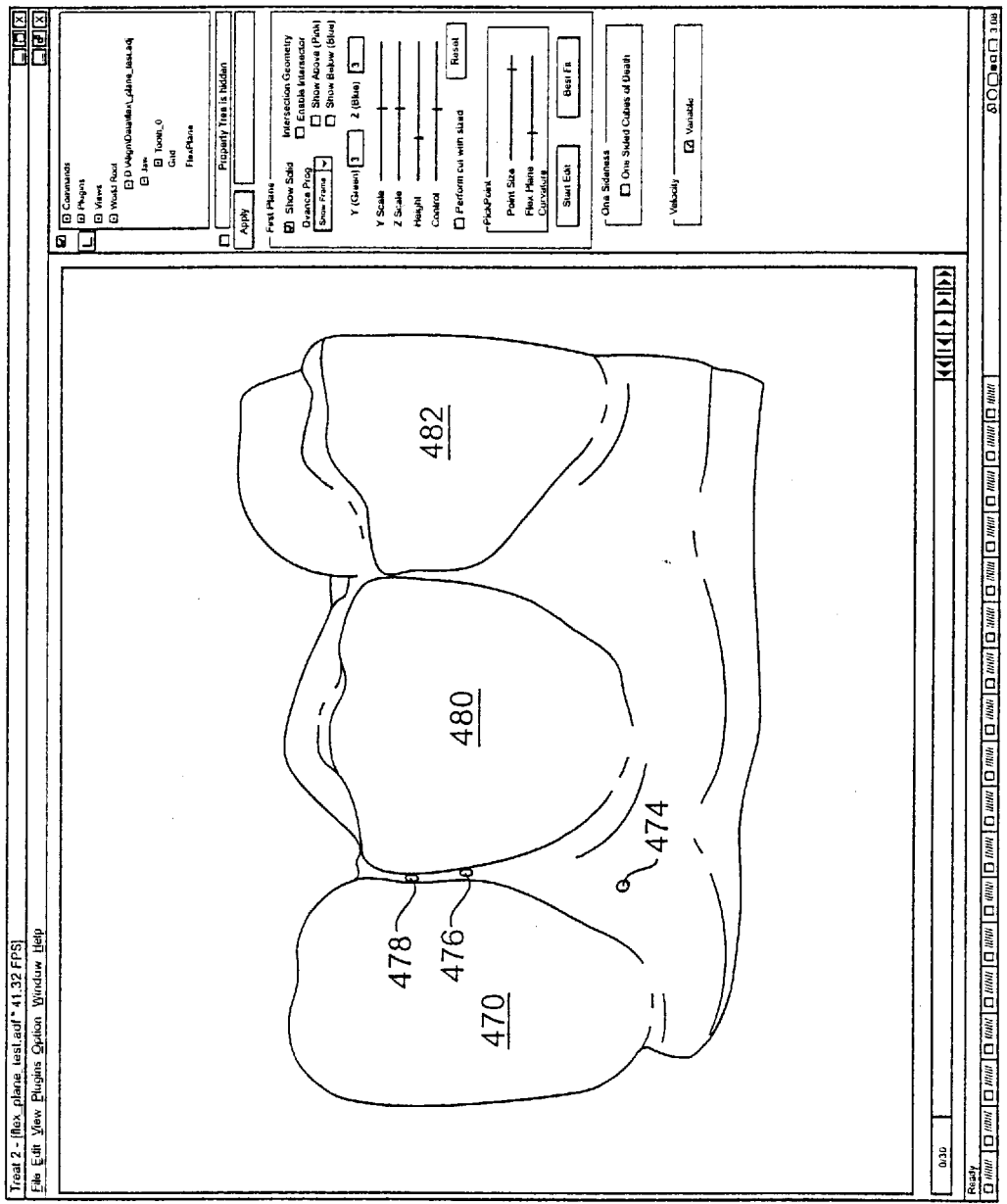
FIGS. 5J–5L show exemplary graphical user interfaces (GUI) for separating the teeth model in accordance with the process of FIG. 5I.
Figure 5K:
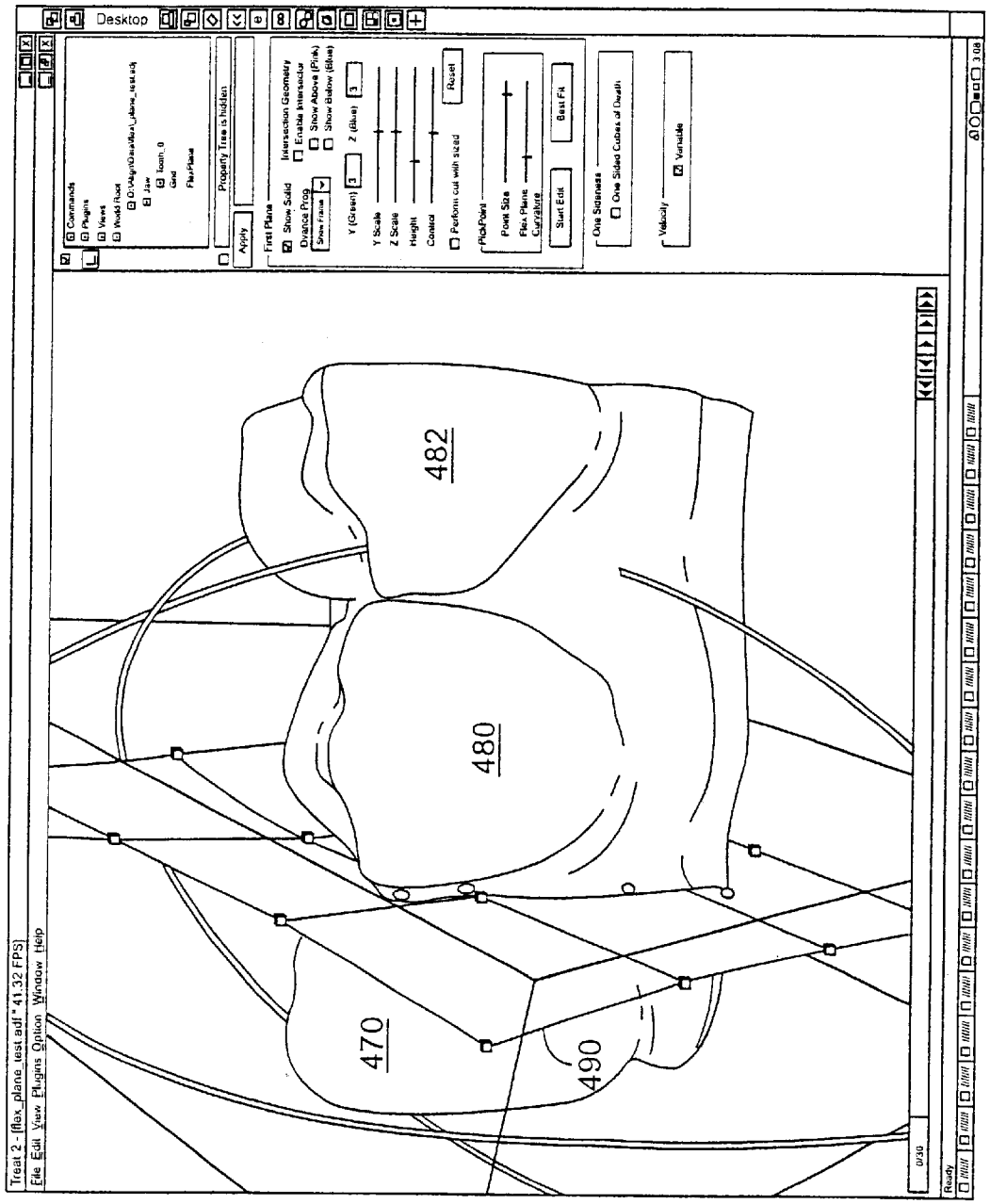
Figure 5L:
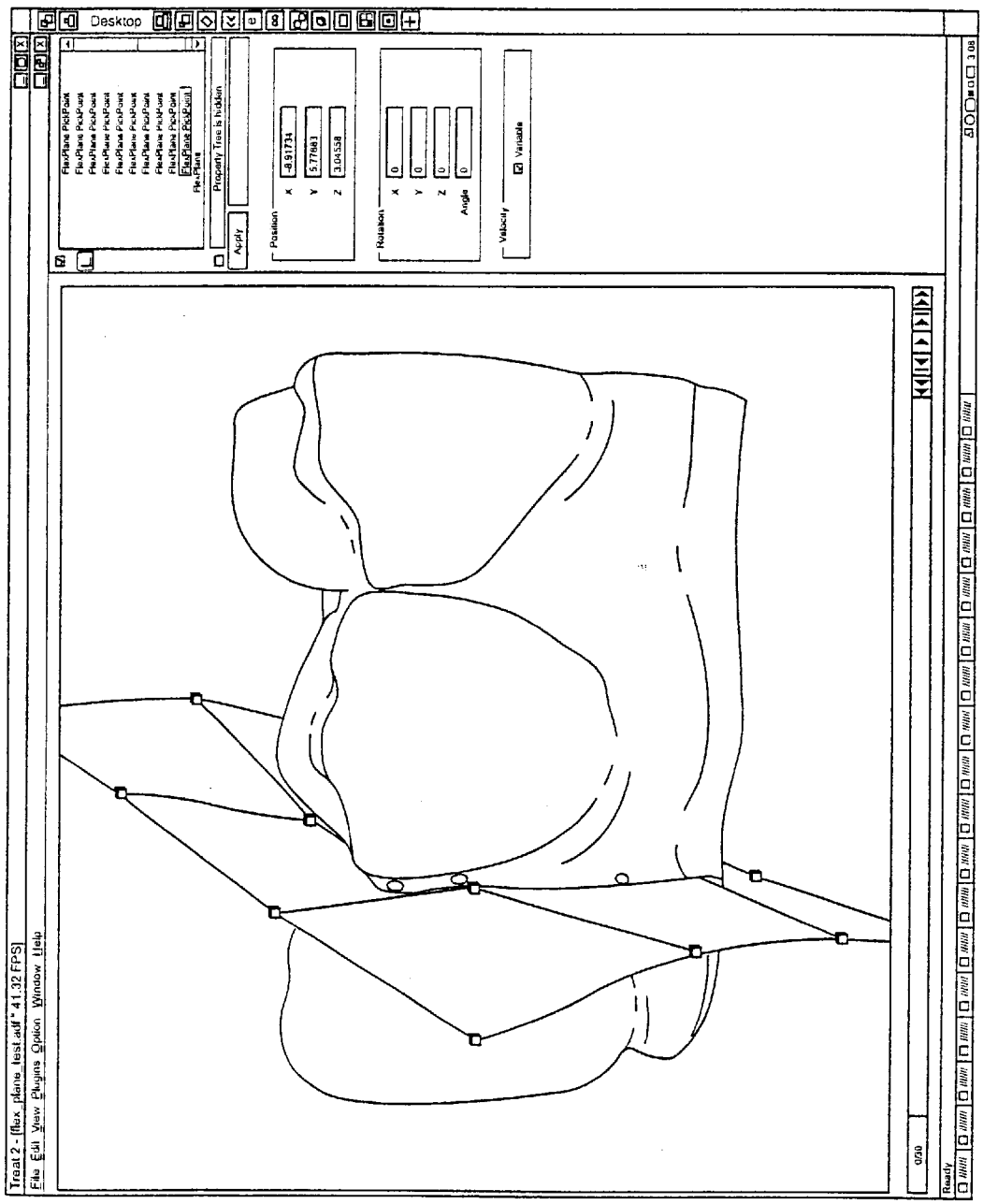

FIGS. 5J–5L show exemplary graphical user interfaces for separating the teeth model in accordance with the process of FIG. 5I. FIG. 5J shows a plurality of teeth 470, 480 and 482. FIG. 5J shows that a user has placed a plurality of markers 474, 476 and 478 indicating the points where the tooth 470 should be cleaved from the teeth 480–482.

FIG. 5K shows that, after determining a best-fit plane that separates the tooth 470 from the tooth 480, a flexible plane 490 is positioned between the tooth 470 and the tooth 480. The flexible plane 490 has a plurality of grid nodes that can be adjusted by the user to better approximate the separation plane between the teeth 470 and 480. The adjusted flexible plane 490 is shown in FIG. 5L.

Figure 6:
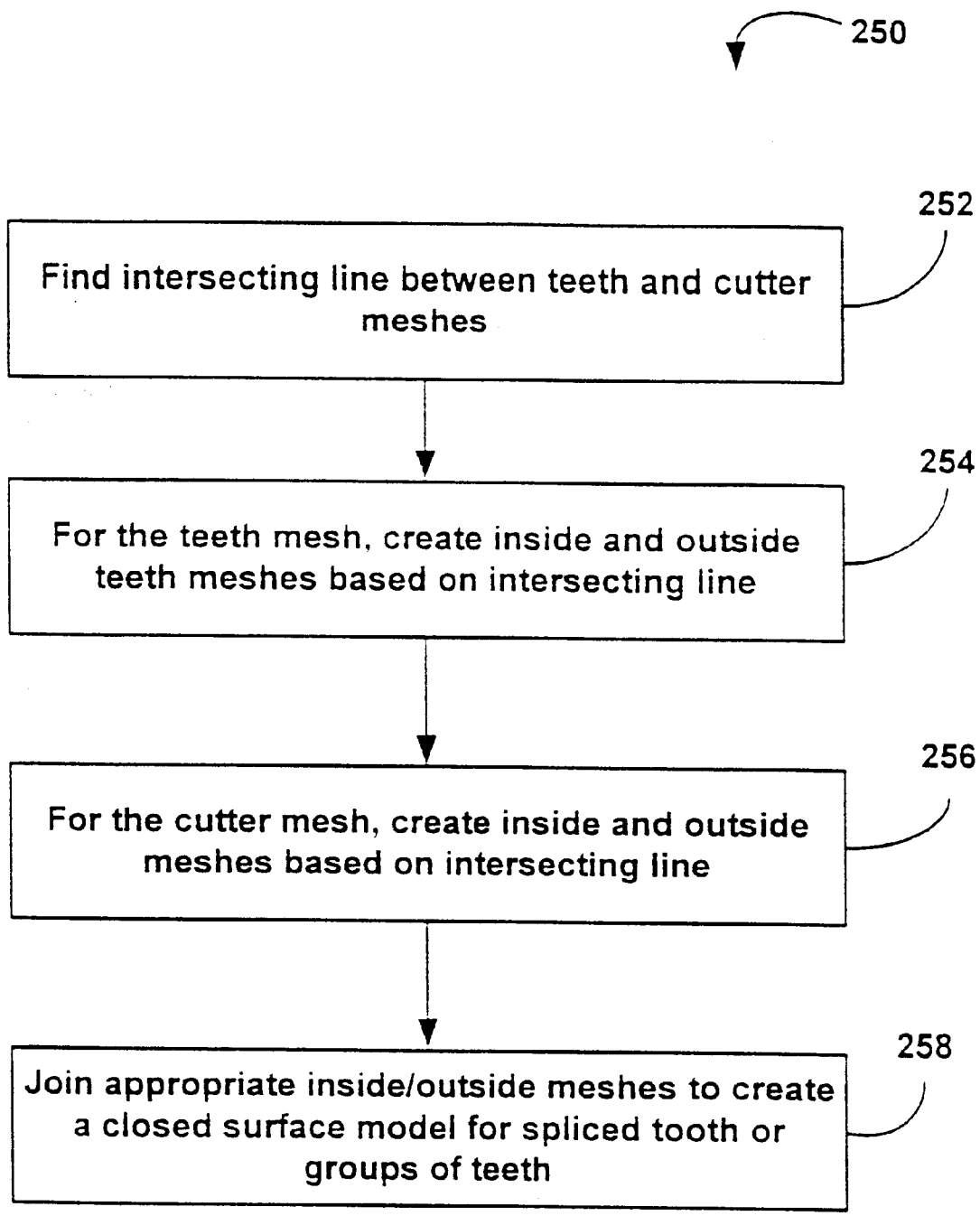
FIG. 6 is a flow chart illustrating a process for splicing two or more teeth at a cutting point.

Referring now to FIG. 6, a process 250 splices a group of teeth into two groups of teeth. First, the process 250 locates an intersecting line between a teeth mesh and a cutter mesh (step 252). Next, for the teeth mesh, the process 250 creates an inside teeth mesh and an outside teeth mesh based on the intersecting line (step 254). Similarly, for the cutter mesh, the process 250 creates an inside mesh, an outside mesh based on the intersecting lines (step 256). Finally, the process 250 joins appropriate inside and outside meshes to create a closed surface model for a spliced tooth or a spliced group of teeth (step 258). Once the closed surface model has been created, the user can continue to manipulate the spliced tooth or groups of teeth as in step 214 of FIG. 5.

Figure 7:
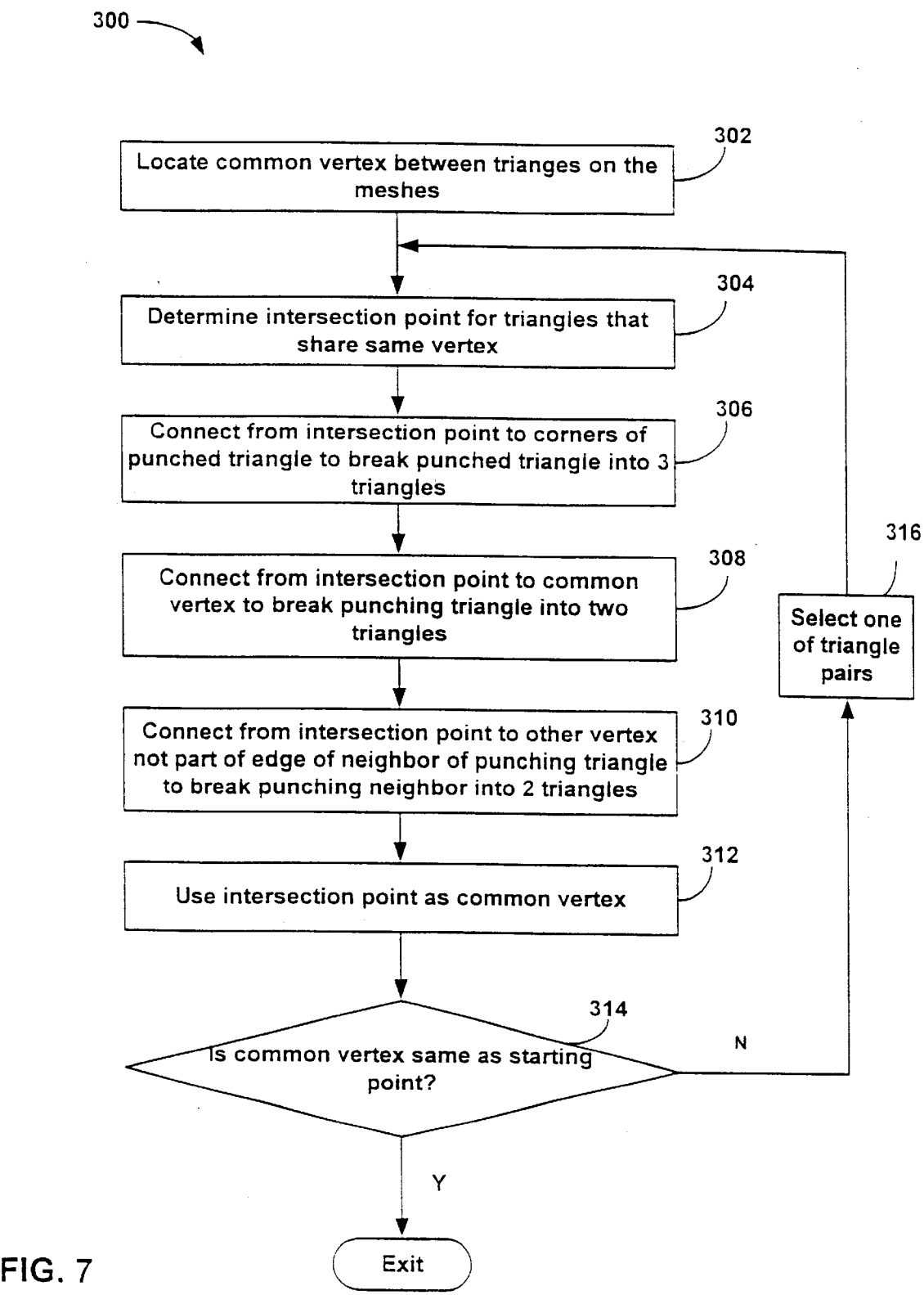
FIG. 7 is a flow chart illustrating in more detail an embodiment of FIG. 6.

FIG. 7 illustrates step 258 of FIG. 6 in more detail. In one embodiment, a process 300 traverses the meshes to identify and generate a closing surface between two teeth or groups of teeth. The closing surface defines a wall that can be applied to the two teeth or groups of teeth after their separation to ensure that the two separated models have enclosed 3D boundaries.

First, the process 300 locates any common vertex between triangles on the appropriate inside/outside meshes (step 302). Next, the process 300 determines an intersecting point for triangles that share the same vertex (step 304). Next, the process connects from the intersection point to the corners of the punched triangle to break the punched triangle into three separate triangles (step 306). In this context, a punched triangle is a triangle through which the edge of the other triangle or the punching triangle goes through.

Next, the process 300 connects from the intersection point to the common vertex to break the punching triangle into two triangles (step 308). Additionally, the process 300 operates on a neighboring triangle of the punching triangle and breaks this triangle up into two triangles (step 310). The process 300 then uses the intersection point as a new common vertex (step 312). The process 300 checks whether the common vertex is the same as the starting vertex (step 314). If not, one of the triangle pairs of the newly generated triangles is selected as a new candidate (step 316) and the process loops back to step 304 to continue this process until the latest new common vertex is the same as the starting point in step 314. If so, the process 300 has traversed the entire surface of the teeth object that needs to be spliced and the process 300 exits. At this point, a new surface defining the closing boundary of the separated teeth group is applied to the original group of teeth to define two new closed surface models of two smaller groups of teeth.

Figure 8A:
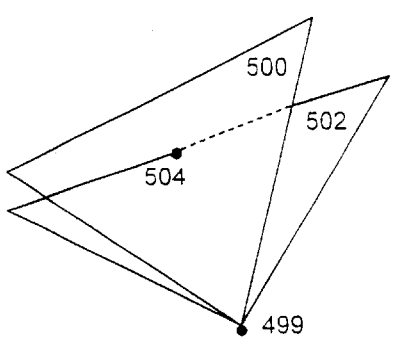
FIG. 8A is an example diagram illustrating two intersecting triangles (punched triangle and punching triangle) with a common vertex.

Referring now to FIGS. 8a through 8d, exemplary operations of the process 300 on two intersecting triangles 500 and 502 are shown. In FIG. 8A, the intersecting triangles 500 and 502 share a common vertex 499 and an intersection point 504. In the context of FIG. 8A, the triangle 500 is the punched triangle while the triangle 502 is the punching triangle.

Figure 8D:
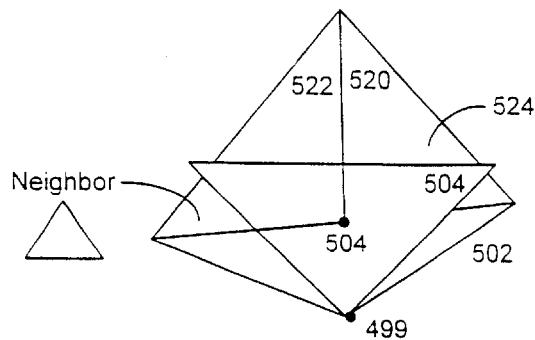
FIG. 8D is an example diagram illustrating the break-up of a neighboring triangle.
Figure 8B:
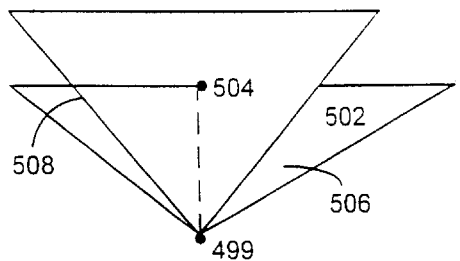
FIG. 8B is an example diagram illustrating the break-up of the punched triangle.
Figure 8C:
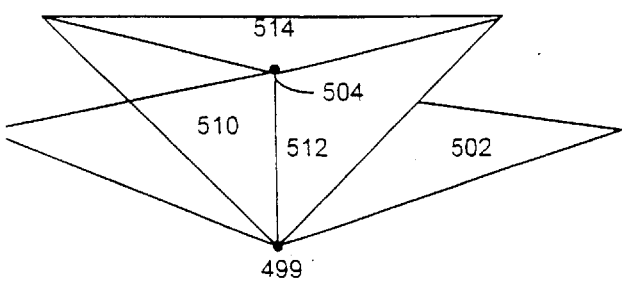
FIG. 8C is an example diagram illustrating the break-up of the punching triangle.

In FIG. 8B, the intersection point of the punched triangle 500 is connected with each corner of the punched triangle 500 to create three new triangles 510, 512, and 514 which shared a common vertex 504. In FIG. 8C, the intersection point 504 is connected to the common vertex of the punched triangle 500 and the punching triangle 502 to break the punching triangle 502 into two triangles 508 and 506. In FIG. 8D, a neighboring triangle 520 of the punching triangle 502 is shown. From the intersection point 504, a line is drawn to the vertex of the neighboring triangle 520 to create two new triangles 522 and 524. In this embodiment, the triangle 522 intersects with at least one of the triangles 510, 512 and 514 or the triangle 524 would intersect with one of the triangles 510, 512 and 514. In a next iteration, the intersection point 504 is then used as a new common vertex and this process repeats itself until it has marched a complete path from the starting point back to itself.

Figure 8E:
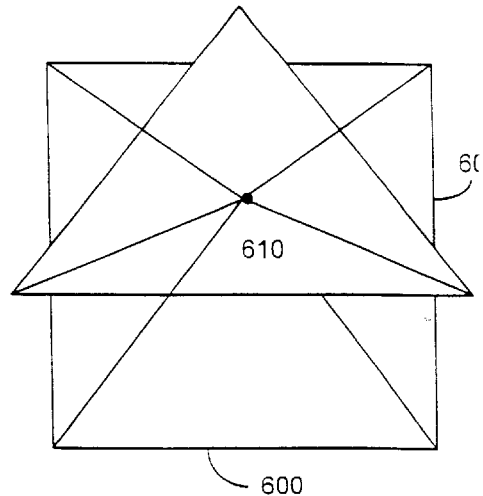
FIG. 8E is an example diagram illustrating two intersecting triangles without a common vertex and the subsequent break-up of the intersecting triangles and a neighboring triangle.

FIG. 8E illustrates one configuration that could be used when triangles do not have a common vertex. In that case, the intersection point of the triangle is used as a common vertex point. FIG. 8E shows two intersecting triangles 600 and 604 that intersect at an intersection point 610. However, the triangle 600 and 604 do not share a common vertex. In this case, the common vertex is the intersection point 610. This point is used to break up the triangle 604 into three separate triangles as discussed previously. Similarly, the intersection point 610 is used to divide the triangles 600 into two smaller triangles. Further, the neighboring triangle 602 is also divided into two smaller triangles based on the intersection point 610.

Figure 9:
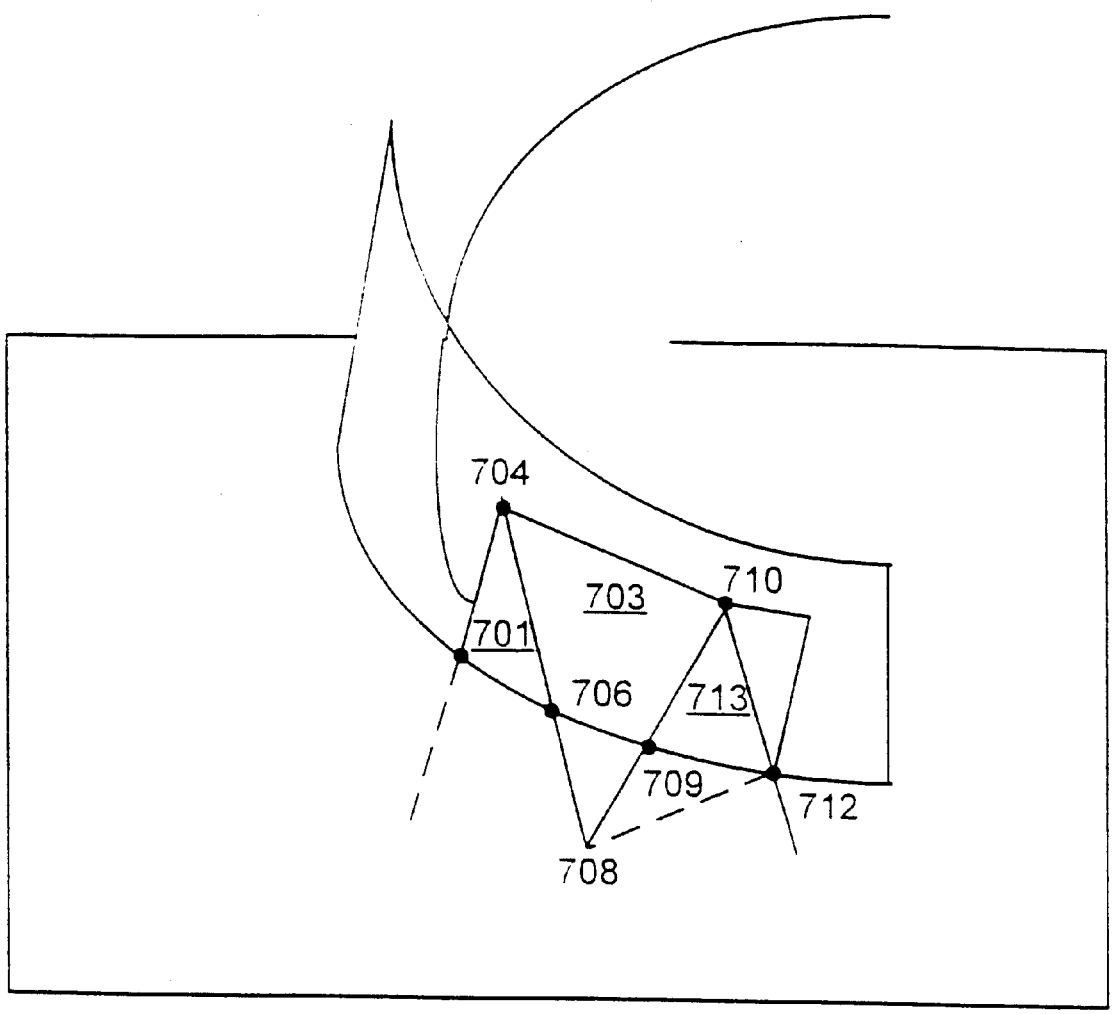
FIG. 9 is diagram illustrating an exemplary traversal of a cutting surface of an exemplary cylinder.

FIG. 9 illustrates one exemplary determination of a new end of an object 700 as defined by cutting surface 708. To simplify, the cutting surface 708 is planar, while the object 700 is a cylindrical object. The cylindrical object 700 is also defined by a plurality of triangle shaped meshes 701, 703, and 713. The traversal of the wall defining a cut in the object 700 starts with node 702. Next, node 706 is found, as well as node 709 and 712. The process continues its determination of triangle meshes until it loops back to point 702 upon which the close end surface of a segmented version of the cylindrical object 700 is determined.

The system can optionally be configured to add roots and hidden surfaces to the tooth models to allow more thorough and accurate simulation of tooth movement during treatment. In alternative implementations, this information is added automatically without human assistance, semi-automatically with human assistance, or manually by human operator, using a variety of data sources.

Figure 10:
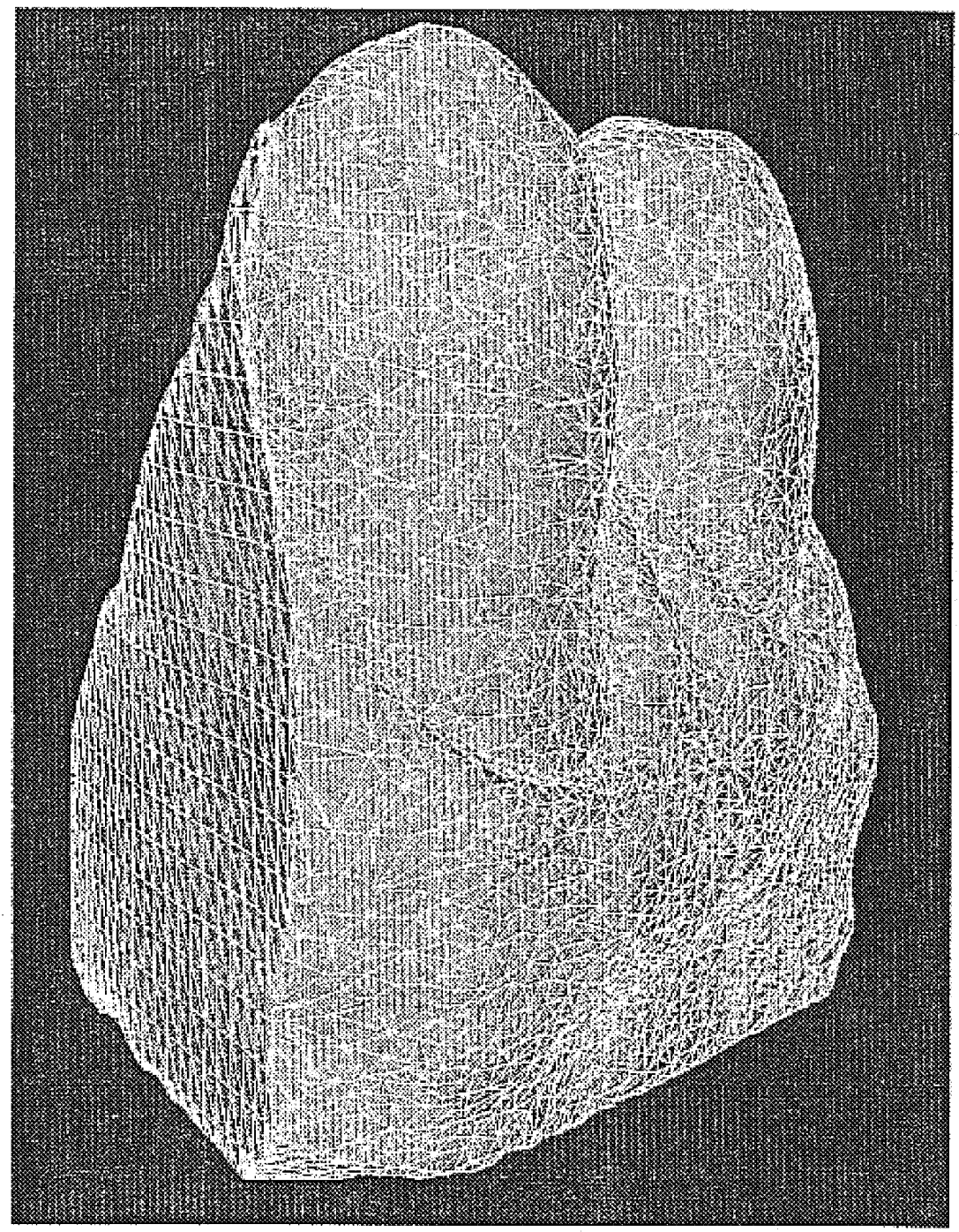
FIG. 10 shows exemplary triangular meshes for a group of teeth separated in accordance with the techniques discussed above.
Figure 11:
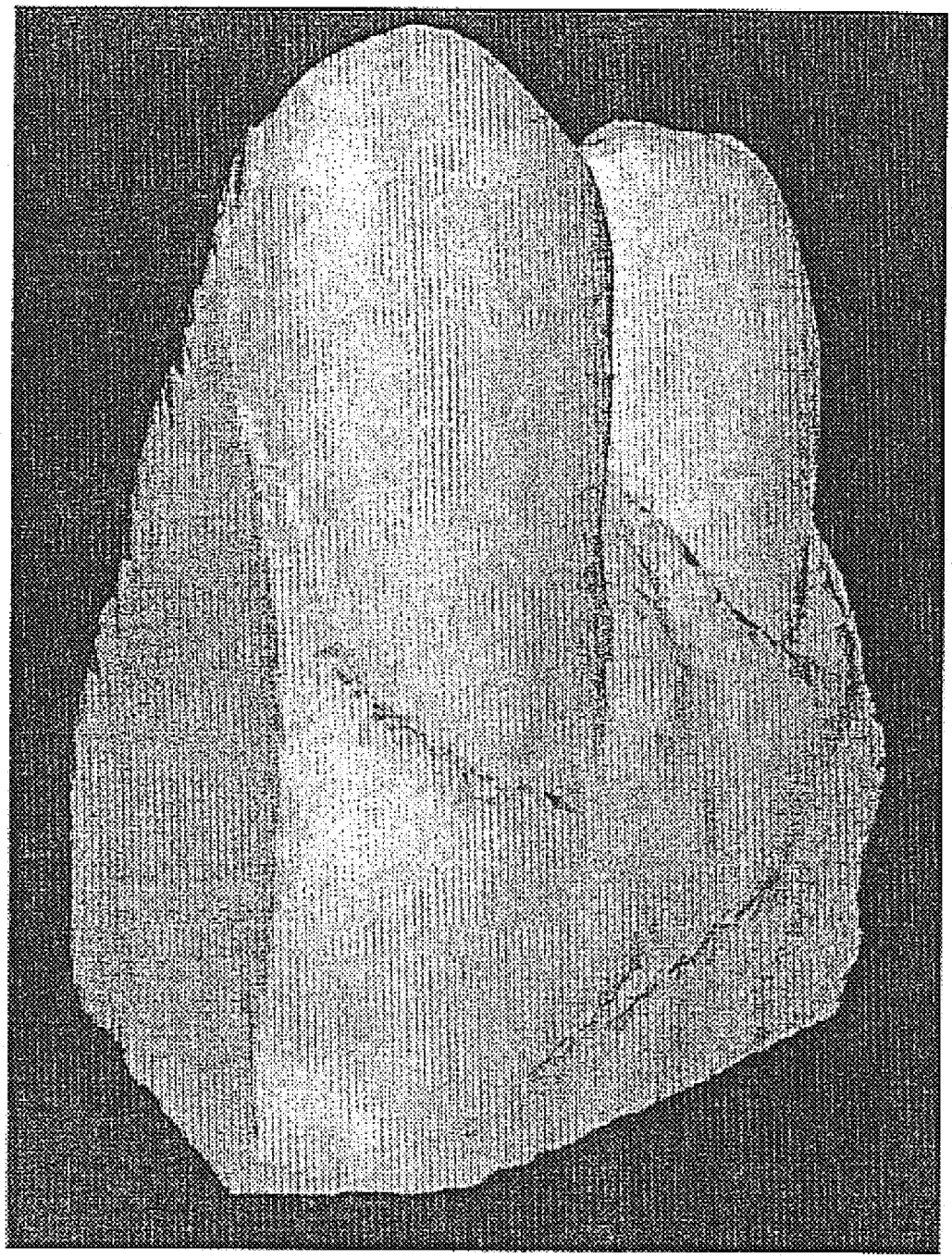
FIGS. 11 and 12 show rendered 3D models of the teeth of FIG. 10.
Figure 12:
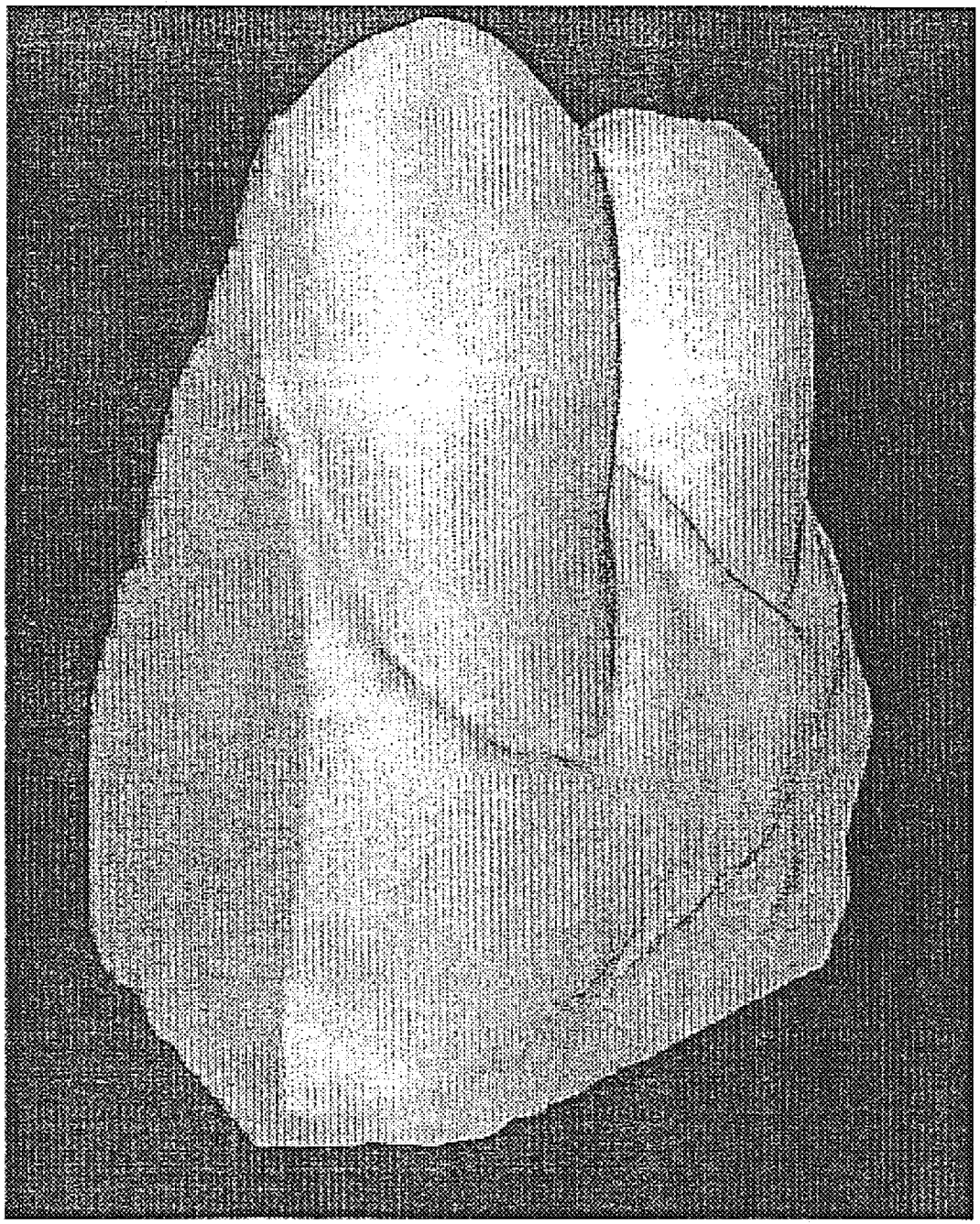

FIG. 10 shows exemplary triangular meshes for a group of teeth separated in accordance with the techniques discussed above, while FIGS. 11 and 12 show exemplary rendered 3D models of the teeth of FIG. 10.

Figure 13:
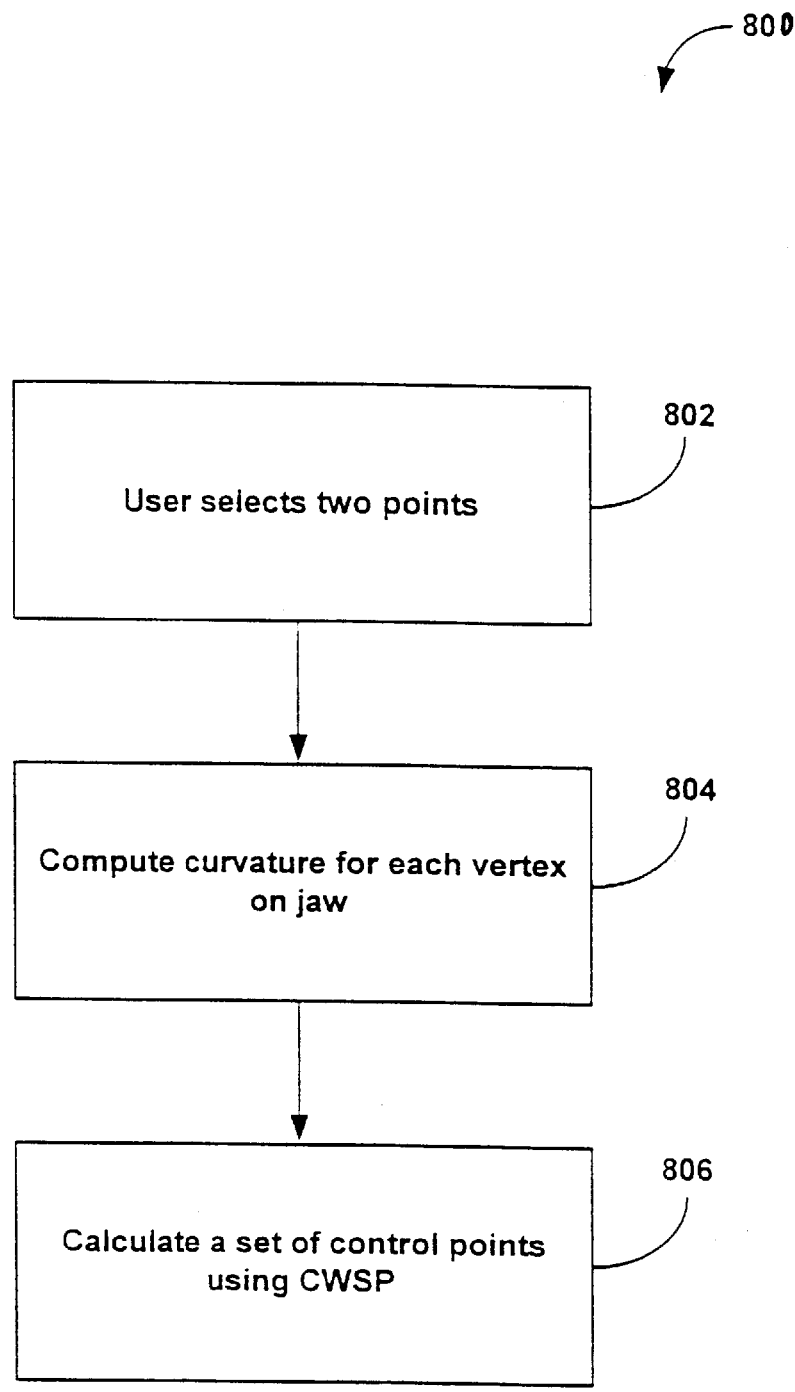
FIG. 13 is a flow chart illustrating a second process for separating two connected objects using two input points.

FIG. 13 shows one process 800 where the control points needed to fit a FlexPlane are calculated using an algorithm called Curvature Weighted Shortest Path (CWSP). The process 800 requires only two input points and automatically calculates a set of control points using CWSP. First, the process accepts two input points from the user (step 802). Next, curvature values are computed for each vertex (step 804) and a set of control points are calculated using CWSP (step 806). Step 804 will be discussed in more detail in FIG. 14, while CWSP will be discussed next.

CWSP uses a graph theoretical technique to find the lowest cost path along edges on a polygonal surface. An undirected graph G [V, E ] consists of a vertex set V and an edge set E where each edge (v,w) is an unordered pair of vertices v and w. A path in a graph from vertex $v_1$ to vertex $v_2$ is a list of vertices $[v_1, v_2, \ldots, v_k]$ such that $(v_{i-1})$ is an edge for i∈[1 . . . k-1]. The path contains vertex vi for i∈[1 . . . k-1] and avoids all other vertices and edges. The path is simple if all its vertices are distinct. The set out(v) contains all the edges that contain v as an endpoint.

The surface is considered to be an undirected graph G, where the vertices of polygons are considered to be the vertices of the graph, and the edges of polygons correspond to edges in the graph. Each edge of G has a cost determined by a cost function (see below). The cost of a path p is the sum of the costs of all the edges on p. A shortest path from a vertex s to a vertex t is a path from s to t whose cost is minimum, that is, there exists no other path from s to t with lower cost. The cost function is the Euclidian distance between the two vertices multiplied by the curvature scaling factor w, as discussed below.

$$cost(v,w)=c|s-t|$$

The values v and w are three-dimensional vectors representing the coordinates of the vertices v and w. The cost is always a positive value, so negative cycles cannot occur. This simplifies the analysis of the shortest path algorithm. In order to find the shortest path from s to t, a shortest path tree is calculated using a modified version of Dijkstra's algorithm. A free tree is an undirected graph that is connected and acyclic. A rooted tree is a free tree T with a distinguished vertex r, called the root. If v and w are vertices such that v is on the path from r to w, v is an ancestor of w. If v and w are adjacent, v is the parent of w, denoted as v=p(w). A spanning tree is a spanning subgraph of G (including all of G's vertices but not necessarily all it edges) that is a tree. A shortest-path tree is a spanning tree rooted at s each of whose paths is a shortest path on G. The complete shortest path tree need not be calculated, since only the shortest path from s to t is needed. Each vertex v in a shortest path tree has a value distance(v) representing the total cost of traversing the path from the root. Computation of the shortest path tree can be halted once t is scanned. The distance to T is a shortest path tree if and only if, for every edge [v,w] in G, distance(v)+cost(v,w)≦distance(w). The process computes distance(v) for every vertex v by processing the vertices in preorder, and then tests the distance inequality for each edge. For each vertex v, the process maintains a tentative distance dist(v) from s to v and a tentative parent p(v) in the shortest path tree. The process initializes dist($\underline{s}$)=0, dist(w)=∞ for v ≠s, p(v)=NULL for all v, and repeat the following step until the distance inequality is satisfied for every edge:

Select an edge [v,w] such that dist(v)+cost(v,w)<dist(w). Replace dist(w) by dist(v)+cost(v,w) and and p(w) by v.

The vertices are partitioned into 3 states: unlabeled, labeled, and scanned. Initially, s is labeled and every other vertex is unlabeled. The following step is repeated until t is scanned: to convert a vertex v to the scanned state, apply the labeling step to each edge [v,w] such that dist(v)+cost(v,w)<dist(w), thereby converting w to the labeled state. An efficient scanning order is Dijkstra's method-among labeled vertices, always scan one whose tentative distance is a minimum. Labeled vertices are stored in a priority queue, which has functions insert (insert a vertex into the queue, sorted) and pop (return the closest vertex & remove from queue). Pseudo-code is below:

```
shortestpathtree( set vertices, vertex source, vertex destination) {
    priority_queue q
    // initialize
    for (each vertex v ∈ vertices){
        dist(v) = ∞
        p(v) = NULL
    }
    boolean endpoint_found = FALSE
    while ( !endpoint_found )    {
        if ( v == destination) {
            endpoint_found = TRUE
            return // break out of loop
        }
        for (edge [v,w] ∈ out(v)) {
            if( dist(v) + cost(v,w) < dist(w) ) {
                dist(w) = dist(v) + cost(v,w)
                p(w) = v
                insert (w,q)
            }
        }
        v = pop(q)
    }
}
```

The computation of the curvature will be discussed next. Give a surface represented by triangle mesh, the process determines the following data at a point P on the surface: principal curvatures, principal directions, Gaussian curvature and mean curvature. Those data will determine the local shape of a surface. The process fits a local parametric surface at point P, then use that parametric surface to compute the curvatures.

Applying a Weingarten Map F as the differential of the Gaussian Map which sends every point P on the surface to a point on the unit sphere determined by the normal vector at P. F is a linear mapping, the following definitions can be made:

Principal curvatures=eigenvalues of F,

Principal directions=eigenvectors of F,

Gaussian curvature=determinant of F,

Mean curvature=trace of F.

So the process finds a matrix representing the Weingarten Map. And all the eigenvalues of F can be calculated from that matrix.

The process will find a local parametric surface S which approximate the TriMesh. Move the TriMesh so that P becomes the origin point and the normal vector at P becomes (0, 0, 1). After this modification, the local parametric surface S can be given as $$z=f(x, y)=a^*x^2+2b^*x^*y+c^*y^2.$$

In this implementation, the process ignores the higher order information since it is irrelevant for curvature computation. The process then finds the Weingarten matrix $$M=\text{matrix } (D, E|E, F).$$

For the parametric surface S, a, b, c approximates D, E, F. The process finds vertices P1, P2, . . . , Pn of the TriMesh which are close to point P. If the coordinate of Pi is (xi, yi, zi), then a, b and c can be calculated by solving the following approximation system of linear equations:

$$z1=a^*x1^2+2b^*x1^*y1+c^*y1^2;$$

. . .

$$zn=a^*xn^2+2b^*xn^*yn+c^*yn^2.$$

The method is a scaling process plus the standard least square method. If the point P is not a vertex of the TriMesh, a linear interpolation is done from the Weingarten matrices of the nearby vertices, and then the curvatures are calculated.

Figure 14:
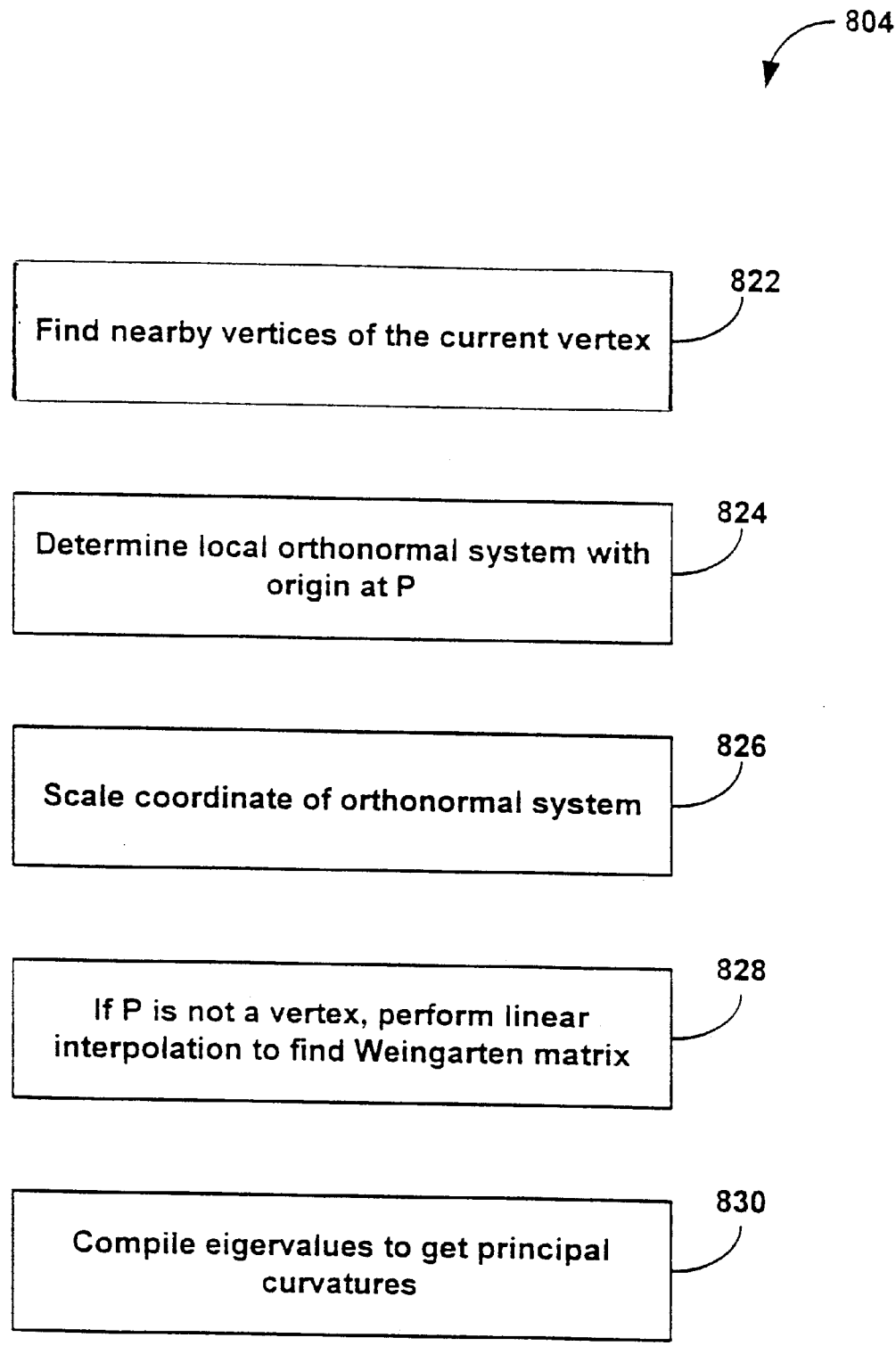
FIG. 14 is a flow chart illustrating a process for computing curvature of each vertex.

FIG. 14 shows in more detail one embodiment of step 804 of FIG. 13. In FIG, 14, for a vertex P, a process 804 performs the following operations:

1. Find the nearby vertices for P (step 822). Here neighbors(edge e, int n) returns all the vertices {P1, P2, . . . , Pn} which can be connected to the vertex P by at most n edges. This is done recursively.

2. Find a local orthonormal coordinate system with origin at P (step 824). The z axis is the surface normal at P. Then the x axis is chosen to be a vector lies on the tangent plane of the surface at P, and choose the y axis. One exemplary way to determine the x axis and y axis is to rotate z axis to the direction (0, 0, 1), then the pull-back of (1, 0, 0) and (0, 1, 0) will provide the x axis and y axis.

3. Scale the coordinates (step 826). Suppose the coordinates of Pi is (xi, yi, zi) in terms of the local coordinate system. Let di=sqrt(xi*xi+yi*yi), and replace (xi, yi, zi) by (ri, si, ti)=(xi/di, yi/di, zi/di).

4. If P is not a vertex, do linear interpolation to find the Weingarten matrix (step 828). In one embodiment, let matrix A, B be given by
A=matrix(r1^2, 2*r1*s1, S1^2|. . . rn ^2, 2*rn*sn, sn^2),
B=matrix(t1|2| . . . |tn).
Let A' denote the transpose of A, and (a, b, c) is given by inverse(A'*A)*B. Then the Weingarten matrix M is approximated by matrix(a, b|b, c).

5. Compute the eigenvalues of M to get the principal curvatures (step 830). Other curvatures can be obtained similarly.

The derivation of the curvature weighting factor is discussed next. The principal curvature p has primary and secondary components $p_1$ and $P_2$. The radius of curvature is represented in millimeters, $p_1$ and $P_2$ are measured in inverse millimeters along the principal directions. A modified curvature M is calculated from the primary curvature added to the absolute value of the secondary curvature:

$$M=p_1+|p_2|$$

The curvature weighting factor w is calculated from M using the stepwise function below:

| Modified Curvature (1/mm) | Curvature Weighting Factor c (unitless) |
| --- | --- |
| M < −0.7 | 1/3 |
| −0.7 < M < 0 | 1/2 |
| 0 < M < 1 | 2 |
| M > 1 | 4 |

The weighting factor c is multiplied by the Euclidian length of an edge to calculate the cost of the edge for the purposes of the shortest path algorithm.

The calculation of control points is discussed next. When picking points for the FlexPlane, the user will place the two control points in or near the embrasures between two teeth on opposite sides of the jaw. The CWSP will pass through the interproximal region between the teeth, and control points will be evenly spaced between them. The Euclidian length of the path is divided by a spacing value (a default of 2 mm is currently used) to determine the number of points to be placed. In addition, a vertical plane that passes through the two initial control points is calculated. The curve representing the intersection of this plane with the jaw surface is then calculated, and additional control points placed along the lower portion of the curve. The FlexPlane fit to these points will in most cases separate the two teeth, although user editing of the FlexPlane may be required to obtain a correct result.

Figure 15:
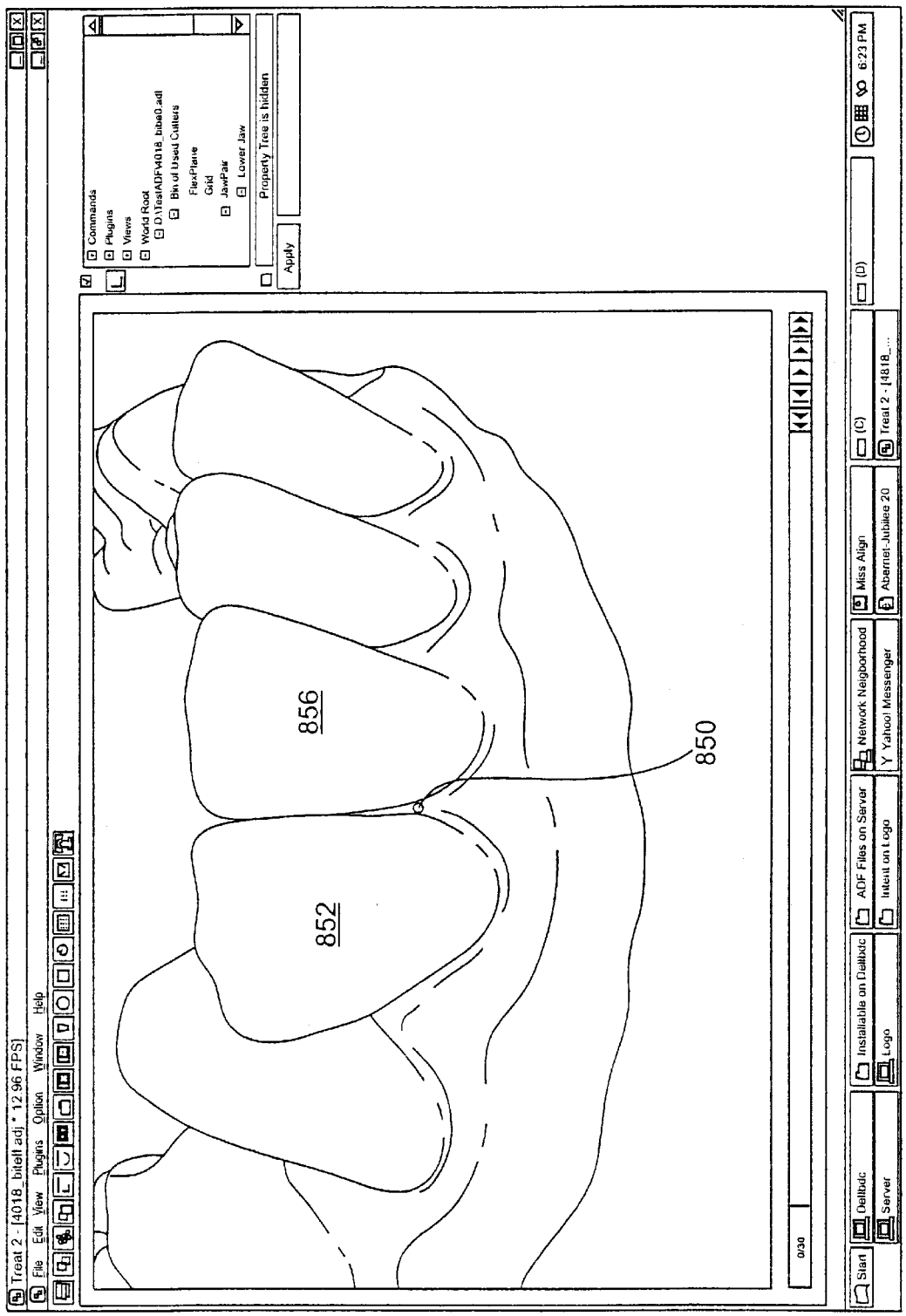
FIGS. 15–17 show an exemplary interface for generating a flexplane separating two adjacent teeth.
Figure 16:
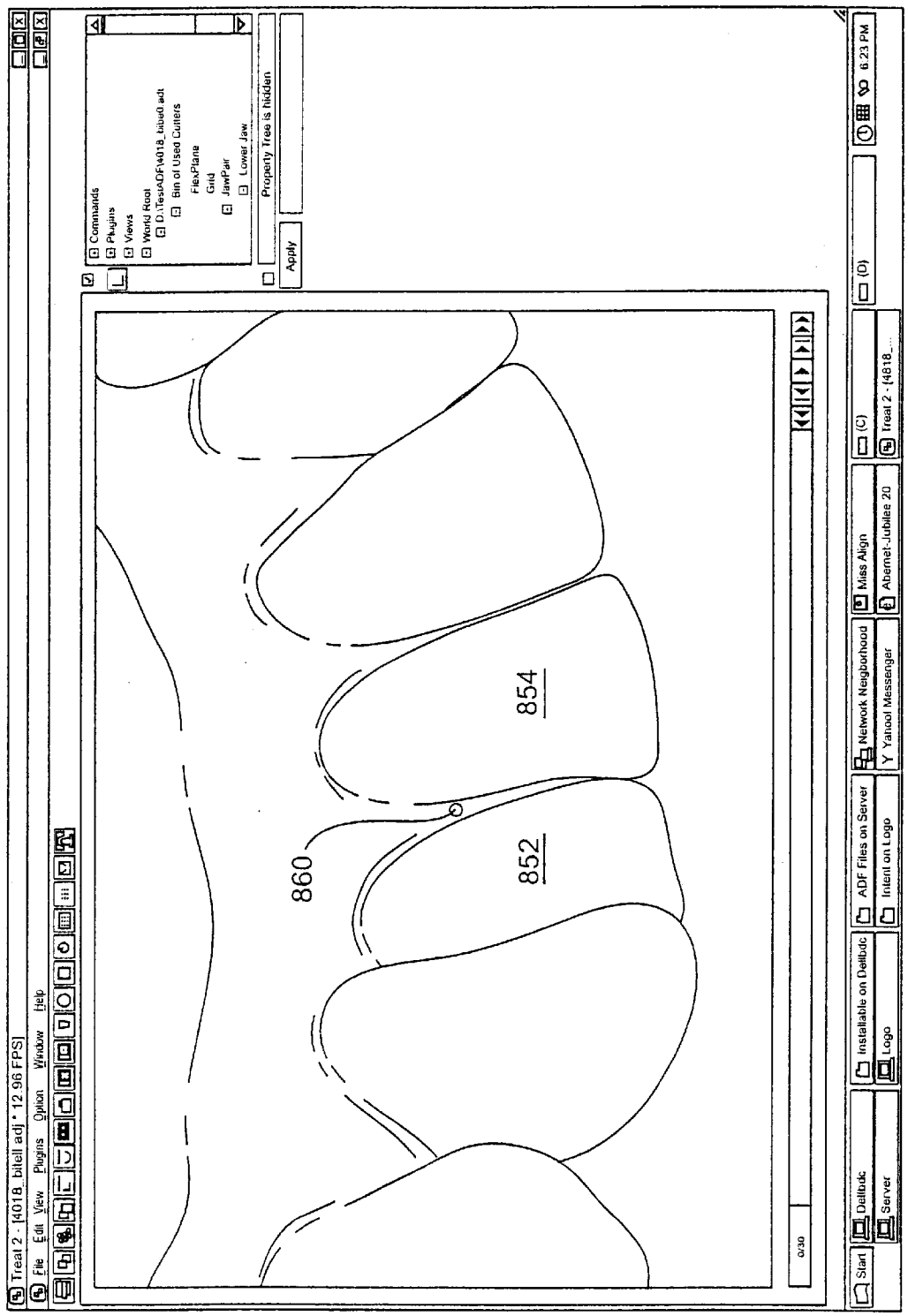
Figure 17:
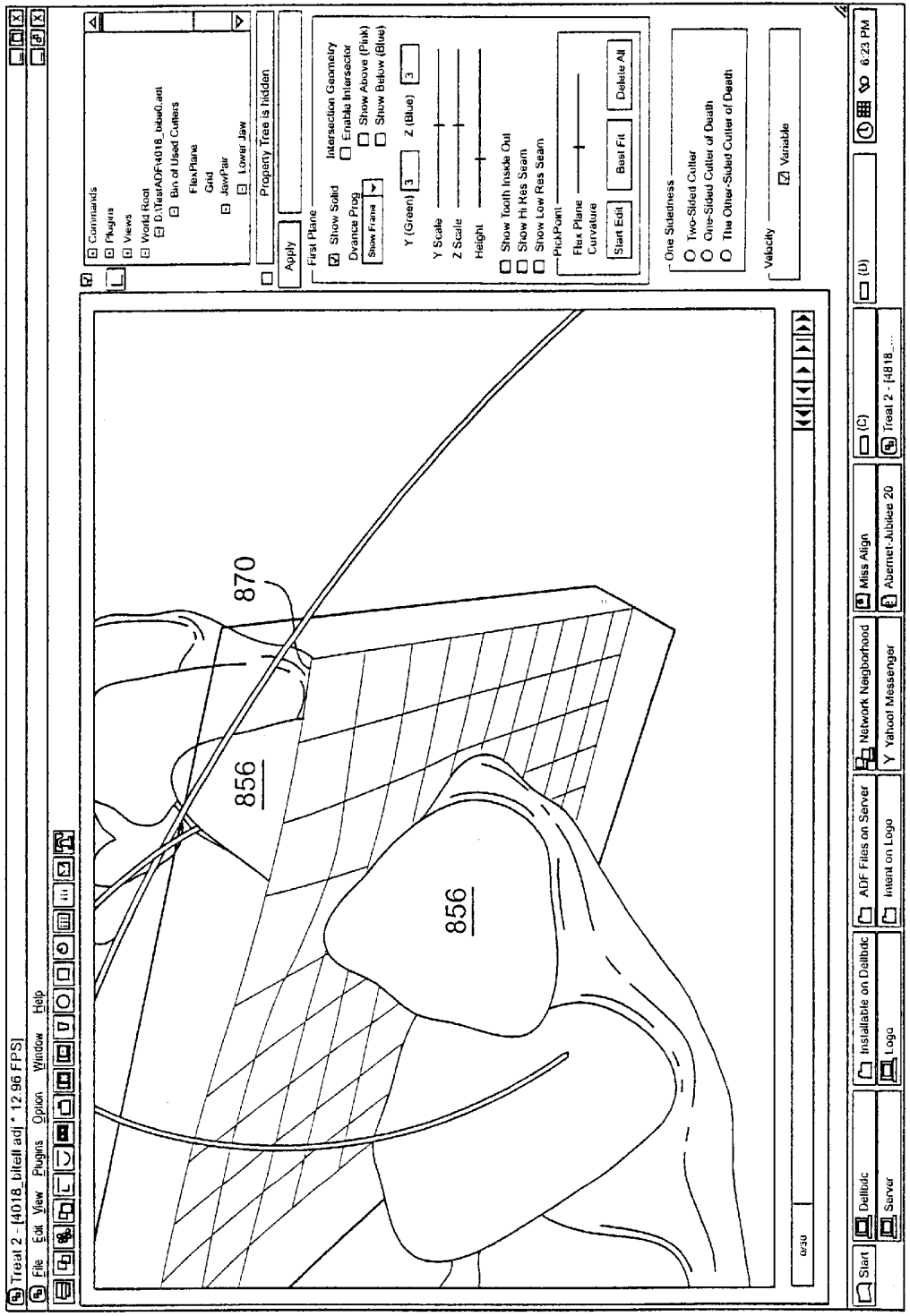

FIGS. 15–17 show exemplary user interfaces for separating two adjacent teeth using only two input points and the processes of FIGS. 13–14. FIG. 15 shows the placement of a first embrasure point 850 along the border of the teeth 852 and 854, while FIG. 16 shows the placement of a second embrasure point 860 on the opposite side of the border between teeth 852 and 854. Applying the processes of FIGS. 13–14, a flex-plane 870 is generated that approximates the border between teeth 852–854 and follows the curvature weighted shortest path between the two embrasure points 852–854. The flex-plane can be used to delineate a cutting plane to separate teeth 852 and 852. As illustrated in FIGS. 15–17, the separation is achieved using one two input points.

Figure 18:
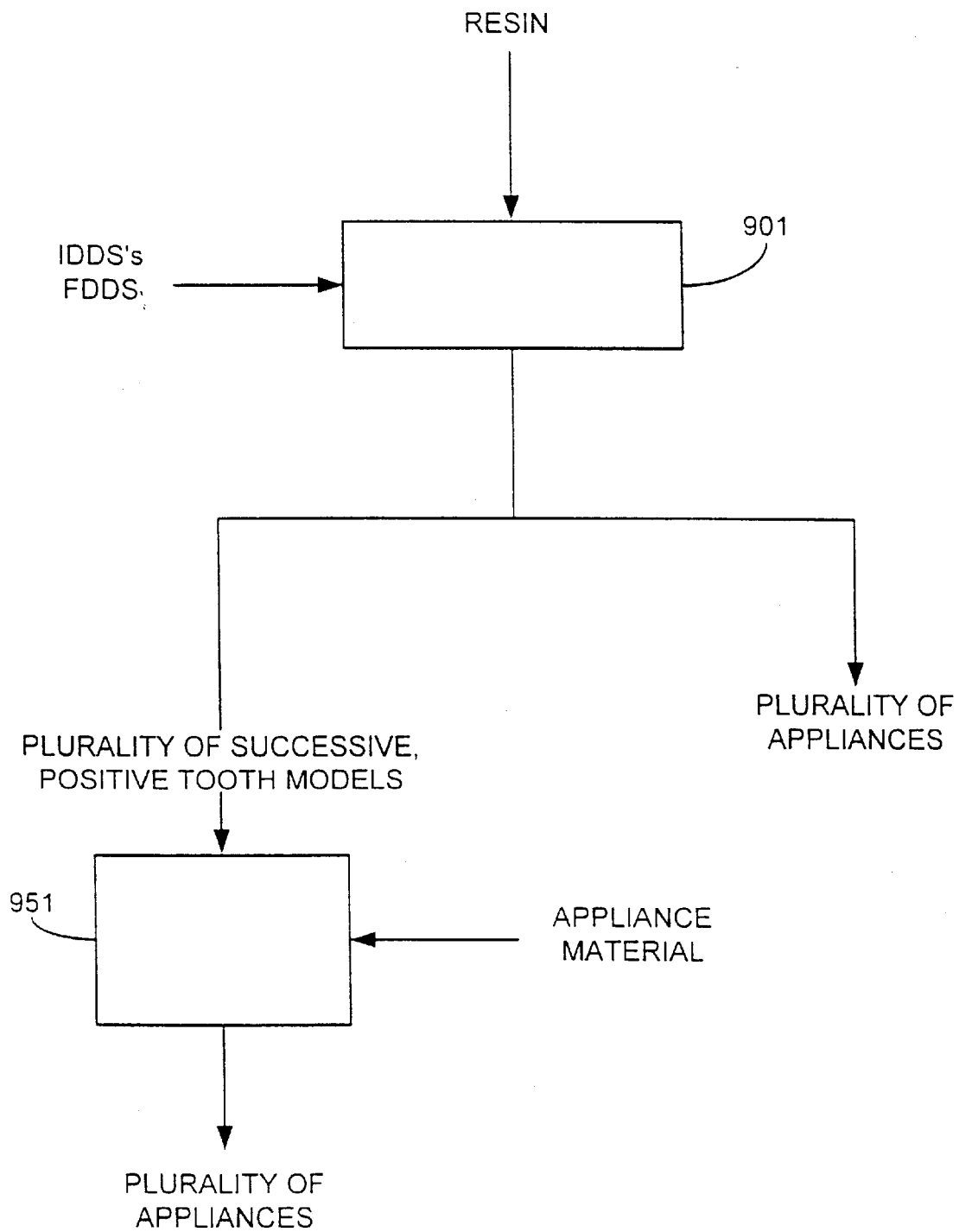
FIG. 18 is a diagram of a system for fabricating appliances.

Once the intermediate and final data sets have been created, the appliances may be fabricated as illustrated in FIG. 18. Common fabrication methods employ a rapid prototyping device 201 such as a stereolithography machine. A particularly suitable rapid prototyping machine is Model SLA-250/50 available from 3D System, Valencia, Calif. The rapid prototyping machine 201 selectively hardens a liquid or other non-hardened resin into a three-dimensional structure which can be separated from the remaining non-hardened resin, washed, and used either directly as the appliance or indirectly as a mold for producing the appliance. The prototyping machine 201 receives the individual digital data sets and produces one structure corresponding to each of the desired appliances. Generally, because the rapid prototyping machine 901 may utilize a resin having non-optimum mechanical properties and which may not be generally acceptable for patient use, the prototyping machine typically is used to produce molds which are, in effect, positive tooth models of each successive stage of the treatment. After the positive models are prepared, a conventional pressure or vacuum molding machine 951 is used to produce the appliances from a more suitable material, such as 0.03 inch thermal forming dental material, available from Tru-Tain Plastics, Rochester, Minn. 55902. Suitable pressure molding equipment is available under the trade name BIO-STAR from Great Lakes Orthodontics, Ltd., Tonawanda, N.Y. 14150. The molding machine 951 produces each of the appliances directly from the positive tooth model and the desired material. Suitable vacuum molding machines are available from Raintree Essix, Inc.

After production, the appliances can be supplied to the treating professional all at one time. The appliances are marked in some manner, typically by sequential numbering directly on the appliances or on tags, pouches, or other items which are affixed to or which enclose each appliance, to indicate their order of use. Optionally, written instructions may accompany the system which set forth that the patient is to wear the individual appliances in the order marked on the appliances or elsewhere in the packaging. Use of the appliances in such a manner will reposition the patient's teeth progressively toward the final tooth arrangement.

Because a patient's teeth may respond differently than originally expected, the treating clinician may wish to evaluate the patient's progress during the course of treatment. The system can also do this automatically, starting from the newly-measured in-course dentition. If the patient's teeth do not progress as planned, the clinician can revise the treatment plan as necessary to bring the patient's treatment back on course or to design an alternative treatment plan. The clinician may provide comments, oral or written, for use in revising the treatment plan. The clinician also can form another set of plaster castings of the patient's teeth for digital imaging and manipulation. The clinician may wish to limit initial aligner production to only a few aligners, delaying production on subsequent aligners until the patient's progress has been evaluated.

Figure 19:
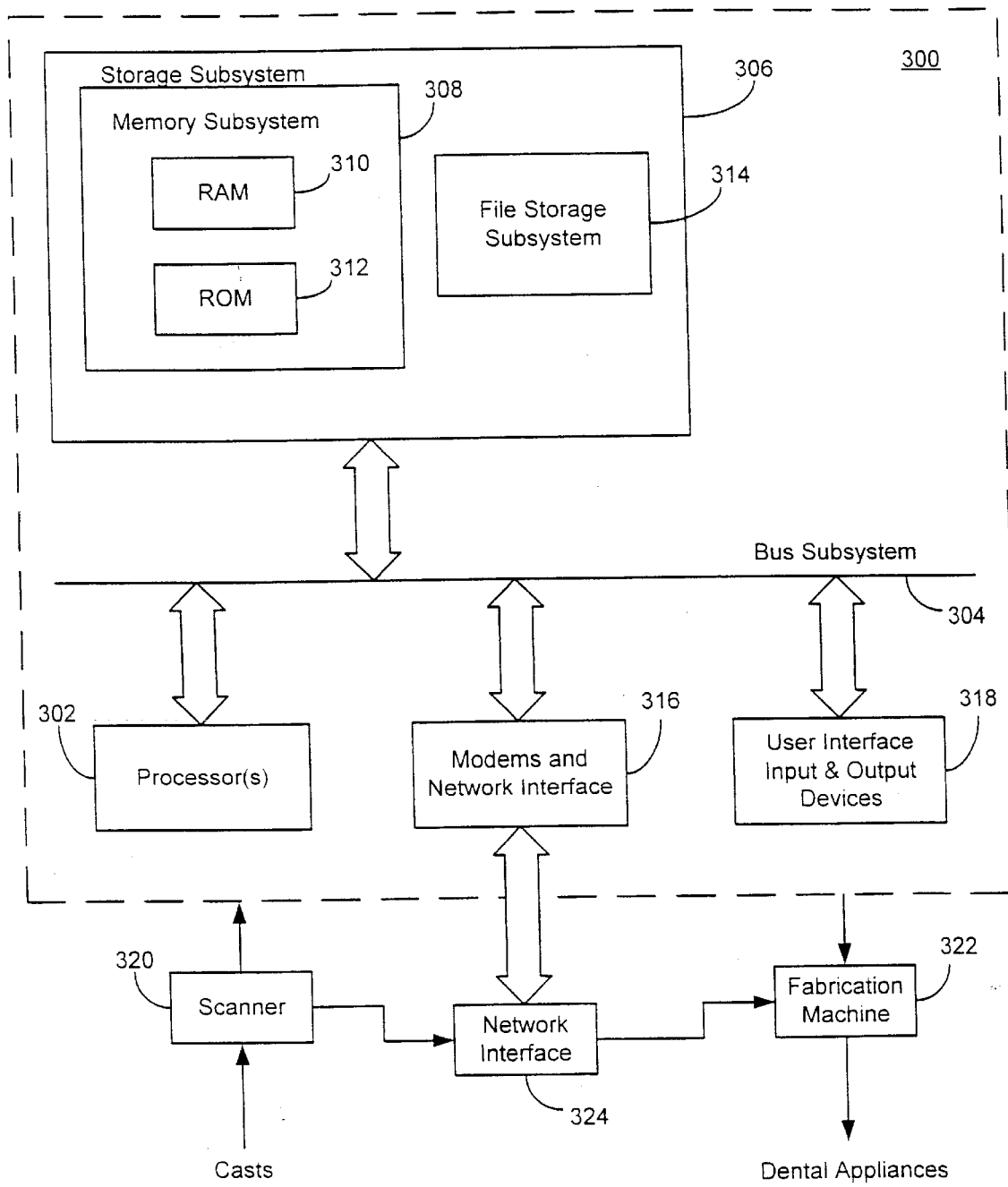
FIG. 19 is a diagram of a computer system supporting the manufacturing of appliances.

FIG. 19 is a simplified block diagram of a data processing system 300 that may be used to develop orthodontic treatment plans. The data processing system 300 typically includes at least one processor 302 that communicates with a number of peripheral devices via bus subsystem 304. These peripheral devices typically include a storage subsystem 306 (memory subsystem 308 and file storage subsystem 314), a set of user interface input and output devices 318, and an interface to outside networks 316, including the public switched telephone network. This interface is shown schematically as "Modems and Network Interface" block 316, and is coupled to corresponding interface devices in other data processing systems via communication network interface 324. Data processing system 300 could be a terminal or a low-end personal computer or a high-end personal computer, workstation or mainframe.

The user interface input devices typically include a keyboard and may further include a pointing device and a scanner. The pointing device may be an indirect pointing device such as a mouse, trackball, touchpad, or graphics tablet, or a direct pointing device such as a touchscreen incorporated into the display, or a three dimensional pointing device, such as the gyroscopic pointing device described in U.S. Pat. No. 5,440,326, other types of user interface input devices, such as voice recognition systems, can also be used.

User interface output devices typically include a printer and a display subsystem, which includes a display controller and a display device coupled to the controller. The display device may be a cathode ray tube (CRT), a flat-panel device such as a liquid crystal display (LCD), or a projection device. The display subsystem may also provide non-visual display such as audio output.

Storage subsystem 306 maintains the basic required programming and data constructs. The program modules discussed above are typically stored in storage subsystem 306. Storage subsystem 306 typically comprises memory subsystem 308 and file storage subsystem 314.

Memory subsystem 308 typically includes a number of memories including a main random access memory (RAM) 310 for storage of instructions and data during program execution and a read only memory (ROM) 312 in which fixed instructions are stored. In the case of Macintosh-compatible personal computers the ROM would include portions of the operating system; in the case of IBM-compatible personal computers, this would include the BIOS (basic input/output system).

File storage subsystem 314 provides persistent (non-volatile) storage for program and data files, and typically includes at least one hard disk drive and at least one floppy disk drive (with associated removable media). There may also be other devices such as a CD-ROM drive and optical drives (all with their associated removable media). Additionally, the system may include drives of the type with removable media cartridges. The removable media cartridges may, for example be hard disk cartridges, such as those marketed by Syquest and others, and flexible disk cartridges, such as those marketed by Iomega. One or more of the drives may be located at a remote location, such as in a server on a local area network or at a site on the Internet's World Wide Web.

In this context, the term "bus subsystem" is used generically so as to include any mechanism for letting the various components and subsystems communicate with each other as intended. With the exception of the input devices and the display, the other components need not be at the same physical location. Thus, for example, portions of the file storage system could be connected via various local-area or wide-area network media, including telephone lines. Similarly, the input devices and display need not be at the same location as the processor, although it is anticipated that personal computers and workstations typically will be used.

Bus subsystem 304 is shown schematically as a single bus, but a typical system has a number of buses such as a local bus and one or more expansion buses (e.g., ADB, SCSI, ISA, EISA, MCA, NuBus, or PCI), as well as serial and parallel ports. Network connections are usually established through a device such as a network adapter on one of these expansion buses or a modem on a serial port. The client computer may be a desktop system or a portable system.

Scanner 320 is responsible for scanning casts of the patient's teeth obtained either from the patient or from an orthodontist and providing the scanned digital data set information to data processing system 300 for further processing. In a distributed environment, scanner 320 may be located at a remote location and communicate scanned digital data set information to data processing system 300 via network interface 324.

Fabrication machine 322 fabricates dental appliances based on intermediate and final data set information received from data processing system 300. In a distributed environment, fabrication machine 322 may be located at a remote location and receive data set information from data processing system 300 via network interface 324.

The invention has been described in terms of particular embodiments. Other embodiments are within the scope of the following claims. For example, the three-dimensional scanning techniques described above may be used to analyze material characteristics, such as shrinkage and expansion, of the materials that form the tooth castings and the aligners. Also, the 3D tooth models and the graphical interface described above may be used to assist clinicians that treat patients with conventional braces or other conventional orthodontic appliances, in which case the constraints applied to tooth movement would be modified accordingly. Moreover, the tooth models may be posted on a hypertext transfer protocol (http) web site for limited access by the corresponding patients and treating clinicians.

What is claimed is:

1. A computer-implemented method for separating a three-dimensional polygonal structure, comprising:
   selecting two points on the structure;
   determining a piece-wise continuous curve on the surface of the structure based on the two points: and
   separating the structure into two objects based on the piece-wise continuous curve.

2. The method of claim 1, wherein the determining a piece-wise continuous curve on the surface of the structure comprises:
   calculating a local curvature for each edge of the structure;
   generating a cost function based on the local curvature and length of the edge; and
   determining the shortest path based on the cost function.

3. The method of claim 2, further comprising generating a set of control points to create a fitting surface based on the shortest path.

4. The method of claim 3 further comprising applying the fitting surface to separate the structure into two portions.

5. The method of claim 4, further comprising interactively highlighting a separated portion.

6. The method of claim 4, further comprising interactively highlighting a border of the portion.

7. The method of claim 3, wherein the fitting surface is expressed as a function.

8. The method of claim 3, wherein the fitting surface is expressed as a spline function.

9. The method of claim 3, wherein the fitting surface is interactively adjusted.

10. The method of claim 3, further comprising determining a shortest path between the points and the fitting surface.

11. The method of claim 3, further comprising minimizing the curvature along the fitting surface.

12. The method of claim 3, wherein the fitting surface is adjusted by moving one or more points on the object.

13. The method of claim 3, wherein the cutting surface is adjusted by moving one or more nodes.

14. The method of claim 3, wherein the cutting surface is adjusted by:
   specifying a point on the cutting surface and between two nodes; and
   adjusting the point to vary the cutting surface.

15. The method of claim 1, wherein the structure comprises one or more teeth.

16. The method of claim 1, wherein the shortest path is used to segment the structure into two portions.

17. The method of claim 1, further comprising:
   displaying a plane having a surface specified by a plurality of nodes;
   adjusting one or more nodes to modify the surface of the plane; and
   applying the plane to the structure.

18. The method of claim 17, further comprising providing a handle to adjust each orientation of the plane.

19. The method of claim 18, wherein adjusting one or more nodes further comprises dragging and dropping the one or more nodes.

20. The method of claim 18, wherein the flexible plane surface is formed using a function applied over a two dimensional plane.

21. The method of claim 20, wherein the function is represented as bicubic Bézier patches.

22. The method of claim 1, wherein the object is two joined teeth to be separated, further comprising:
   receiving an initial digital data set representing the two joined teeth,
   representing the two joined teeth as a teeth mesh;
   applying a fitting surface to the teeth mesh;
   identifying an intersecting line between the teeth mesh and fitting surface; and
   generating two separated teeth based on the intersecting line.

23. The method of claim 22, further comprising rendering a three-dimensional (3D) graphical representation of the separated teeth.

24. The method of claim 22, further comprising receiving an instruction from a human user to modify the graphical representation of the teeth and modifying the graphical representation in response to the instruction.

25. A computer program, residing on a tangible storage medium, for use in determining a piece-wise continuous curve on the surface of a three-dimensional polygonal structure, the program comprising executable instructions operable to cause a computer to:

compute a local curvature for each edge of the object;

generate a cost function based on the local curvature and length of the edge; and determine the shortest path based on the cost function.

26. A method for use in separating a computer model of teeth, the method comprising performing the following steps on a computer having at least one processor and memory:

receiving a data set that contains a 3D representation of one or more teeth, calculating a local curvature for each edge of the teeth;

generating a cost function based on the local curvature and length of the edge;

determining the shortest path by minimizing the cost function;

determining a fitting surface for the shortest path; and applying the fitting surface to the teeth to separate the teeth.

27. A computer-implemented method to separate first and second portions of a tooth, comprising:

defining a cutting surface intersecting the first and second portions by specifying two points on the tooth; and applying the cutting surface to the tooth to separate the tooth into two portions.

28. The method of claim 27, wherein defining a cutting surface further comprises:

calculating a local curvature for each edge of the tooth;

generating a cost function based on the local curvature and length of the edge;

determining the shortest path by minimizing the cost function; and fitting the cutting surface based on the shortest path.

29. The method of claim 27, further comprising:

calculating a local curvature for each edge of the structure;

generating a cost function based on the local curvature and length of the edge; and determining the shortest path based on the cost function.

30. The method of claim 29, further comprising generating a set of control points to create a fitting surface based on the shortest path.

31. The method of claim 30 further comprising applying the fitting surface to separate the structure into two portions.

32. The method of claim 31, wherein the fitting surface is expressed as a function.

33. The method of claim 31, wherein the fitting surface is expressed as a spline function.

34. The method of claim 30, wherein the fitting surface is interactively adjusted.

35. The method of claim 34, further comprising interactively highlighting a separated portion.

* * * * *